United States Patent [19]
Hargraves et al.

[11] Patent Number: 6,013,270
[45] Date of Patent: Jan. 11, 2000

[54] SKIN CARE KIT

[75] Inventors: Peter James Hargraves, Cincinnati, Ohio; Julie Elizabeth Wilson, Philadelphia, Pa.; Christopher Irwin; Timothy John Fowler, both of Cincinnati, Ohio; Robert Bao Kim Ha, Milford, Ohio

[73] Assignee: The Procter & Gamble Company, Cincinnati, Ohio

[21] Appl. No.: 09/063,324

[22] Filed: Apr. 20, 1998

[51] Int. Cl.$^7$ ............................... A61K 6/00; A61K 7/00
[52] U.S. Cl. ............................................ 424/401; 514/937
[58] Field of Search ............................... 424/401; 514/937

[56] References Cited

U.S. PATENT DOCUMENTS

| | | | |
|---|---|---|---|
| 3,861,946 | 1/1975 | Waitkins et al. | 117/100 B |
| 4,820,518 | 4/1989 | Murphy et al. | 424/401 |
| 4,875,604 | 10/1989 | Czech | 222/257 |
| 5,068,056 | 11/1991 | Robb | 252/313.1 |
| 5,082,660 | 1/1992 | Ounanian et al. | 424/63 |
| 5,122,418 | 6/1992 | Nakane et al. | 424/401 |
| 5,188,831 | 2/1993 | Nicoll et al. | 424/401 |
| 5,215,580 | 6/1993 | Elfenthal et al. | 106/441 |
| 5,223,250 | 6/1993 | Mitchell et al. | 424/59 |
| 5,223,559 | 6/1993 | Arraudeau et al. | 524/47 |
| 5,366,660 | 11/1994 | Tapley | 252/309 |
| 5,443,759 | 8/1995 | Dahms | 252/302 |
| 5,468,471 | 11/1995 | Zecchino et al. | 424/59 |
| 5,476,660 | 12/1995 | Somasundaran et al. | 424/401 |
| 5,516,457 | 5/1996 | Dahms | 252/302 |
| 5,531,985 | 7/1996 | Mitchell et al. | 424/59 |
| 5,545,399 | 8/1996 | Lee et al. | 424/59 |
| 5,587,148 | 12/1996 | Mitchell et al. | 424/59 |
| 5,587,170 | 12/1996 | Caisey et al. | 424/401 |
| 5,607,504 | 3/1997 | Schmid et al. | 106/403 |
| 5,618,522 | 4/1997 | Kaleta et al. | 424/60 |
| 5,643,555 | 7/1997 | Collin et al. | 424/59 |
| 5,693,329 | 12/1997 | Marchi-Lemann et al. | 424/401 |
| 5,700,451 | 12/1997 | Yue et al. | 424/59 |
| 5,733,531 | 3/1998 | Mitchnick et al. | 424/59 |

FOREIGN PATENT DOCUMENTS

| | | |
|---|---|---|
| 0 293 795 A1 | 12/1988 | European Pat. Off. ......... A61K 7/48 |
| 0 502 769 A1 | 9/1992 | European Pat. Off. ......... A61K 7/48 |
| 0 504 066 A1 | 9/1992 | European Pat. Off. . |
| 0 708 154 A2 | 10/1994 | European Pat. Off. .......... C09C 1/62 |
| 245815 A1 | 5/1987 | Germany ....................... A61K 7/021 |
| 62-209011 | 9/1987 | Japan ............................... A61K 7/02 |
| 7-330536 | 12/1995 | Japan ............................... A61K 7/00 |

(List continued on next page.)

OTHER PUBLICATIONS

Derwent Abstract No. 92–302056/37; Date Sep. 9, 1992; Country Europe (abstract of Doc. #26 above).
"Quantification of the Soft–Focus Effect," Emmert, Dr. Ralf, *Cosmetics & Toiletries*, vol. 111, Jul. 1996, pp. 57–61.
Chemical Abstract No. 94–188868/23; Date Oct. 20, 1992; Country Japan (abstract of JP 06–128,122 A).
Chemical Abstract No. 96–388694/39; Date Jan. 9, 1995; Country Japan (abstract of JP 08–188,723 A).

(List continued on next page.)

*Primary Examiner*—Thurman K. Page
*Assistant Examiner*—S. Howard
*Attorney, Agent, or Firm*—Loretta J. Henderson; Armina E. Mathews; George W. Allen

[57] ABSTRACT

The present invention relates to a skin care kit useful skin conditioning. The kit, which includes a skin care composition contained within a dispenser, is particularly useful for providing good moisturization and aesthetics to both cream and lotion users. More particularly, this invention relates to a skin care kit useful for regulating skin condition (especially human skin, more especially human facial skin), including lubricating the skin, increasing the smoothness and suppleness of the skin, preventing or relieving dryness of the skin, hydrating the skin, and/or protecting the skin regulating visible and/or tactile discontinuities in skin, e.g., visible and/or tactile discontinuities in skin texture, more especially discontinuities associated with skin aging.

30 Claims, 4 Drawing Sheets

FOREIGN PATENT DOCUMENTS

| | | | |
|---|---|---|---|
| 8-073316 | 3/1996 | Japan | A61K 7/02 |
| 8-073317 | 3/1996 | Japan | A61K 7/02 |
| 1112193 | 5/1965 | United Kingdom | A61K 7/00 |
| 2 280 605 | 2/1995 | United Kingdom | A61K 7/021 |
| 2 291 804 | 2/1996 | United Kingdom | A61K 7/02 |
| 2 300 629 | 11/1996 | United Kingdom | C09C 3/12 |
| 93/18852 | 9/1993 | WIPO | B01J 13/00 |
| 93/23482 | 11/1993 | WIPO | C09C 3/08 |
| 94/06406 A1 | 3/1994 | WIPO | A61K 7/48 |
| 94/09756 | 5/1994 | WIPO | A61K 7/48 |
| 94/15580 | 7/1994 | WIPO | A61K 7/42 |
| 96/03964 | 2/1996 | WIPO | A61K 7/00 |
| 96/07396 A2 | 3/1996 | WIPO | A61K 7/48 |
| 96/19180 | 6/1996 | WIPO | A61K 7/100 |

OTHER PUBLICATIONS

Derwent Abstract No. 96–450843; Date Sept. 3, 1996; (abstract of JP 08 225 316 A).

Patent Abstracts of Japan, Publication No.: 07267824, Cosmetic Compounded With Organic–Inorganic Composite Pigment, Oct. 17, 1995.

KOBO Products, Inc., Product List Technical Data (4 pp.), Feb. 1996.

KOBO Products, Inc., New Dispersions (10 pp.), Feb. 1996.

Ahlnäs, "Zeta Potential: An Important Aspect in Formulating", Kemira Technical Seminar, Oct. 3, 1994.

Tambe et al., "Factors Controlling the Stability of Colloid–Stabilized Emulsions", *J. of Colloid and Interface Science*, vol. 157, pp. 244–253 (1993).

Lee et al., "Preparation of Ultrafine $Fe_3O_4$ Particles by Precipitation in the Presence of PVA at High pH", *J. of Colliod and Interface Science*, vol. 177, pp. 490–494 (1996).

SKIN CARE KIT

TECHNICAL FIELD

The present invention relates to the field of conditioning skin care compositions and dispensers therefor. More particularly, this invention relates to a skin care kit comprising a pump dispenser and a composition useful for regulating skin condition (especially human skin, more especially human facial skin), including lubricating the skin, increasing the smoothness and suppleness of the skin, preventing or relieving dryness of the skin, hydrating the skin, and/or protecting the skin regulating visible and/or tactile discontinuities in skin, e.g., visible and/or tactile discontinuities in skin texture, more especially discontinuities associated with skin aging.

BACKGROUND

In the skin care market, there are two defined consumer user groups, namely cream users and lotion users. Cream users desire a skin care product of relatively high viscosity (i.e., thick consistency) that provides good moisturization. Lotion users, in contrast, desire a skin care product of relatively low viscosity (i.e., thinner consistency) which also provides good moisturization but yet which is absorbed quickly into the skin upon topical application. Traditionally, skin care product manufacturers have recognized the unique needs of the two distinct consumer groups and have marketed both a cream and lotion version of the same product in order to satisfy both groups. This categorical product distinction, however, is inefficient and increases the manufacturer's costs to develop, test, scale-up and market the product. These costs are inevitably passed on to the consumers. Therefore, there remains a need for a single topical skin care product which provides good aesthetic and skin conditioning benefits which appeal to both cream and lotion consumer user groups.

In addition to compositions which appeal to both cream and lotion users, it is important that such compositions are marketed in suitable packaging that also appeals to both user groups. An important factor that is often neglected in packaging is the ergonomic factor. Both cream and lotion users desire product packaging that is easy and comfortable to use. Yet, due to the nature of the different product forms, creams are typically marketed in jars or tubes with relatively large orifices while lotions are typically marketed in pumps, bottles or tubes with relatively smaller orifices. Thus, both user groups are predisposed to purchase the types of packages which are typically associated with their respective products. Despite this predisposition, cream users still prefer that their thicker skin care product be dispensed with the accuracy of a pump. Therefore, there is a need for a single dispenser which is ergonomically friendly and efficient such that the skin care product is dispensed easily and comfortably and such that the number of dispenser components is minimal.

It has surprisingly been found that the present invention provides a single skin care product which appeals to both cream and lotion users by satisfying these needs. The present inventors have found that a single skin care product consisting of particular skin care compositions contained in defined dispensers provide the skin conditioning and aesthetic benefits desired by both cream and lotion users.

The present invention also relates to methods of regulating skin condition by topical application of the present skin care compositions contained therein.

SUMMARY OF THE INVENTION

The present invention relates to a skin care kit comprising a skin care composition contained within a dispenser. The skin care composition of the present invention is useful for topical application and for providing skin conditioning. In particular, the compositions regulate skin condition which includes, but is not limited to, lubricating the skin, increasing the smoothness and suppleness of the skin, preventing or relieving dryness of the skin, hydrating the skin, and/or protecting the skin regulating visible and/or tactile discontinuities in skin, e.g., visible and/or tactile discontinuities in skin texture, more especially discontinuities associated with skin aging. The skin care composition comprises an emulsion having: 1) at least one hydrophobic phase comprising an oil and from about 0.1% to about 20% of a light emollient; 2) at least one hydrophilic phase comprising water; and 3) from about 0.1% to about 5% of an emulsifier having an HLB of at least 6. The composition also has a viscosity of from about 15,000 cps to about 200,000 cps and a pH of from about 3 to about 9. Preferably, the skin care composition of the present invention comprises:

1) an oil-in-water emulsion with:
   a) at least one hydrophobic phase comprising an oil and from about 0.15% to about 10% of a light emollient selected from the group consisting of isohexadecane, isopropyl isostearate, methyl isostearate, ethyl isostearate, isononyl isonononoate, dimethicone, and mixtures thereof;
   b) at least one hydrophilic phase comprising water,
   c) from about 0.1% to about 5% of an emulsifier selected from the group consisting of sorbitan monostearate, sucrose cocoate, steareth-10, steareth-20, steareth-21, steareth-100, oleth-10, oleth-20, laureth-23, cetearyl glucoside, ceteth-10, ceteth-20, PEG-100 stearate, and mixtures thereof; and
   d) from about 0.1% to about 5%, by weight of the composition, of a polymeric thickening agent;
2) from about 0.1% to about 2% of a reflective particulate material which is preferably charged and is selected from the group consisting of $TiO_2$, ZnO, $ZrO_2$, and mixtures thereof, and
3) from about 0.1% to about 20% of a skin care active, preferably niacinamide, wherein the composition has a viscosity of from about 25,000 cps to about 60,000 cps and a pH of from about 5 to about 7.

The dispenser for the skin care composition comprises a manually-operated pump fixedly connected to an ergonomic container having an actuator cap wherein the dispenser is configured such that the pump is in register with the container and the container is shaped so as to provide for comfortable and easy gripping by a human hand, wherein the hand readily conforms to the shape of the container and the actuator cap may be depressed substantially solely by movement of the tip of either the thumb or index finger. In preferred embodiments, the dispenser is configured as shown in the accompanying drawings.

BRIEF DESCRIPTION OF THE DRAWINGS

Embodiments of the invention shall now be described by way of example with reference to the accompanying drawings, wherein.

DETAILED DESCRIPTION OF THE INVENTION

Figure 1:
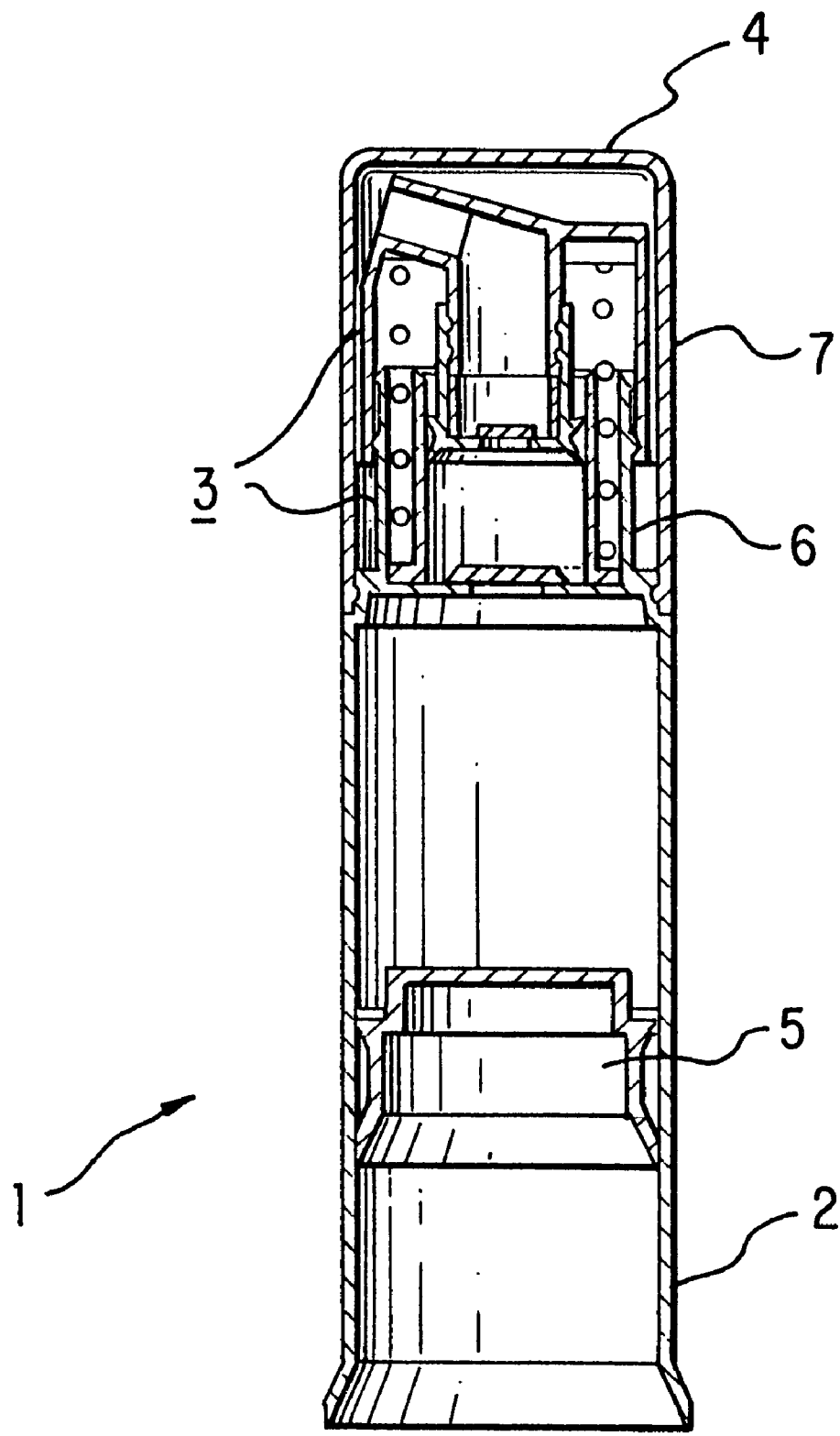
FIG. 1 shows a longitudinal sectional view of a dispenser according to a first embodiment of the invention.

All percentages and ratios used herein are by weight of the total composition, and all measurements made are at 25° C., unless otherwise designated.

The compositions of the present invention can comprise, consist essentially of, or consist of, the essential as well as optional ingredients and components described herein. As used herein, "consisting essentially of" means that the composition or component may include additional ingredients, but only if the additional ingredients do not materially alter the basic and novel characteristics of the claimed compositions or methods.

All publications cited herein are hereby incorporated by reference in their entirety. The term "topical application", as used herein, means to apply or spread the compositions of the present invention onto the surface of the skin.

The term "dermatologically-acceptable," as used herein, means that the compositions or components thereof so described are suitable for use in contact with human skin without undue toxicity, incompatibility, instability, allergic response, and the like.

The term "safe and effective amount" as used herein means an amount of a compound, component, or composition sufficient to significantly induce a positive benefit, preferably a positive skin appearance or feel benefit, including independently the benefits disclosed herein, but low enough to avoid serious side effects, i.e., to provide a reasonable benefit to risk ratio, within the scope of sound medical judgment.

Active and other ingredients useful herein may be categorized or described herein by their cosmetic and/or therapeutic benefit or their postulated mode of action. However, it is to be understood that the active and other ingredients useful herein can in some instances provide more than one cosmetic and/or therapeutic benefit or operate via more than one mode of action. Therefore, classifications herein are made for the sake of convenience and are not intended to limit an ingredient to the particularly stated application or applications listed.

The compositions of the invention are useful for topical application and for providing skin conditioning (i.e., moisturization) following application of the composition to the skin. More particularly, the compositions of the present invention are useful for regulating skin condition, including regulating visible and/or tactile discontinuities in skin, including but not limited to visible and/or tactile discontinuities in skin texture and/or color, more especially discontinuities associated with skin aging. Such discontinuities may be induced or caused by internal and/or external factors. Extrinsic factors include ultraviolet radiation (e.g., from sun exposure), environmental pollution, wind, heat, low humidity, harsh surfactants, abrasives, and the like. Intrinsic factors include chronological aging and other biochemical changes from within the skin.

Regulating skin condition includes prophylactically and/or therapeutically regulating skin condition. As used herein, prophylactically regulating skin condition includes delaying, minimizing and/or preventing visible and/or tactile discontinuities in skin. As used herein, therapeutically regulating skin condition includes ameliorating, e.g., diminishing, minimizing and/or effacing, such discontinuities. Regulating skin condition involves improving skin appearance and/or feel, e.g., providing a smoother, more even appearance and/or feel. As used herein, regulating skin condition includes regulating signs of aging. "Regulating signs of skin aging" includes prophylactically regulating and/or therapeutically regulating one or more of such signs (similarly, regulating a given sign of skin aging, e.g., lines, wrinkles or pores, includes prophylactically regulating and/or therapeutically regulating that sign).

"Signs of skin aging" include, but are not limited to, all outward visibly and tactilely perceptible manifestations as well as any other macro or micro effects due to skin aging. Such signs may be induced or caused by intrinsic factors or extrinsic factors, e.g., chronological aging and/or environmental damage. These signs may result from processes which include, but are not limited to, the development of textural discontinuities such as wrinkles, including both fine superficial wrinkles and coarse deep wrinkles, skin lines, crevices, bumps, large pores (e.g., associated with adnexal structures such as sweat gland ducts, sebaceous glands, or hair follicles), scaliness, flakiness and/or other forms of skin unevenness or roughness, loss of skin elasticity (loss and/or inactivation of functional skin elastin), sagging (including puffiness in the eye area and jowls), loss of skin firmness, loss of skin tightness, loss of skin recoil from deformation, discoloration (including undereye circles), blotching, sallowness, hyperpigmented skin regions such as age spots and freckles, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues, especially those proximate to the skin.

It is to be understood that the present invention is not to be limited to regulation of the above mentioned "signs of skin aging" which arise due to mechanisms associated with skin aging, but is intended to include regulation of said signs irrespective of the mechanism of origin. As used herein, "regulating skin condition" is intended to include regulation of such signs irrespective of the mechanism of origin.

I. Emulsion

The compositions of the present invention comprise an emulsion within which the essential materials and optional materials are incorporated to enable the essential materials and optional components to be delivered to the skin at an appropriate concentration. The emulsion can thus act as a diluent, dispersant, solvent, or the like for the other composition components which ensues that the composition can be applied to and distributed evenly over the selected target at an appropriate concentration.

Suitable emulsions include conventional or otherwise known carriers that are dermatologically acceptable. The emulsion components should also be physically and chemically compatible with the essential components described herein, and should not unduly impair stability, efficacy or other use benefits associated with the compositions of the present invention. Preferred components of the emulsions of this invention should be capable of being comingled in a manner such that there is no interaction which would substantially reduce the efficacy of the composition under ordinary use situations.

Preferred emulsions comprise a hydrophilic phase comprising a hydrophilic component, e.g., water or other hydrophilic diluent, and a hydrophobic phase comprising a hydrophobic component, e.g., a lipid, oil or oily material. As well known to one skilled in the art, the hydrophilic phase will be dispersed in the hydrophobic phase, or vice versa, to form respectively hydrophilic or hydrophobic dispersed and continuous phases, depending on the composition ingredients. In emulsion technology, the term "dispersed phase" is a term well-known to one skilled in the art which means that the phase exists as small particles or droplets that are suspended in and surrounded by a continuous phase. The dispersed phase is also known as the internal or discontinuous phase. The emulsion may be or comprise (e.g., in a triple or other multi-phase emulsion) an oil-in-water emulsion or a water-in-oil emulsion such as a water-in-silicone emulsion. Oil-in-water emulsions of the present compositions preferably comprise from about 1% to about 50% (preferably about 1% to about 30%) of the dispersed hydrophobic phase and from about 1% to about 98% (preferably from about 40% to about 90%) of the continuous hydrophilic phase; water-in-oil emulsions preferably comprise from about 1% to about 98%, more preferably from about 40% to about 90%, of the dispersed hydrophilic phase and from about 1% to about 50%, more preferably 1% to about 30% of the continuous hydrophobic phase. The emulsion may also comprise a gel network, such as described in G. M. Eccleston, "Application of Emulsion Stability Theories to Mobile and Semisolid O/W Emulsions," *Cosmetics & Toiletries,* Vol. 101, November 1996, pp. 73–92. Oil-in-water emulsions are preferred.

Preferred compositions have an apparent viscosity of from about 15,000 to about 200,000 centipoise (cps), preferably about 20,000 to about 100,000 cps, more preferably about 25,000 to about 60,000 cps. Viscosity can be determined using a Brookfield RVDV-II digital viscometer, a T-C spindle (Spindle 93, 27.1 mm crossbar length), at 5 rpm, or the equivalent thereof. Prior to viscosity measurement, the composition is allowed to stabilize following its preparation or any agitation which results from handling. Generally, stabilization should last at least 24 hours under conditions of 25° C. +/−1° C. and ambient pressure. In further preparation for viscosity measurements, the compositions are placed in containers which will produce no or only minimal frictional effects on the viscosity determination (e.g., a 2 oz. glass jar with an orifice of at least 28 mm). The viscosity is measured with the composition at a temperature of 25° C. +/−1° C. and after 30 seconds of spindle rotation. Five (5) viscosity measurements are gathered and the mean of the measurements is calculated in order to determine the viscosity of the composition.

The compositions of the present invention are preferably formulated to have a pH of from about 3 to about 9, more preferably about 4 to about 8, even more preferably about 5 to about 7, and most preferably about 6.25 to about 7.

A. Hydrophobic Phase

Emulsions according to the present invention contain a hydrophobic phase comprising a lipid, oil, oily or other hydrophobic component and from about 0.1% to about 20% of a light emollient. The compositions of the present invention preferably comprise from about 1% to about 50%, preferably from about 1% to about 30%, and more preferably from about 1% to about 10% by weight of the composition of a hydrophobic component. The hydrophobic component may be derived from animals, plants, or petroleum and may be natural or synthetic (i.e., man-made). Preferred hydrophobic components are substantially water-insoluble, more preferably essentially water-insoluble. Preferred hydrophobic components are those having a melting point of about 25° C. or less under about one atmosphere of pressure, and are suitable for conditioning the skin.

Nonlimiting examples of suitable hydrophobic components include those selected from the group consisting of:

1) Mineral oil

Mineral oil, which is also known as petrolatum liquid, is a mixture of liquid hydrocarbons obtained from petroleum. See The Merck Index, Tenth Edition, Entry 7048, p. 1033 (1983) and International Cosmetic Ingredient Dictionary, Fifth Edition, vol. 1, p.415–417 (1993).

2) Petrolatum

Petrolatum, which is also known as petroleum jelly, is a colloidal system of nonstraight-chain solid hydrocarbons and high-boiling liquid hydrocarbons, in which most of the liquid hydrocarbons are held inside the micelles. See The Merck Index, Tenth Edition, Entry 7047, p. 1033 (1983); Schindler, *Drug. Cosmet. Ind.*, 89, 36–37, 76, 78–80, 82 (1961); and International Cosmetic Ingredient Dictionary, Fifth Edition, vol. 1, p. 537 (1993).

3) Straight and branched chain hydrocarbons having from about 7 to about 40 carbon atoms Nonlimiting examples of these hydrocarbon materials include dodecane, isododecane, squalane, cholesterol, hydrogenated polyisobutylene, docosane (i.e. a $C_{22}$ hydrocarbon), hexadecane, isohexadecane (a commercially available hydrocarbon sold as Permethyl® 101A by Presperse, South Plainfield, N.J.). Also useful are the $C_7$–$C_{40}$ isoparaffins, which are $C_7$–$C_{40}$ branched hydrocarbons.

4) $C_1$–$C_{30}$ alcohol esters of $C_1$–$C_{30}$ carboxylic acids and of $C_2$–$C_{30}$ dicarboxylic acids including straight and branched chain materials as well as aromatic derivatives (as used herein in reference to the hydrophobic component, mono- and poly- carboxylic acids include straight chain, branched chain and aryl carboxylic acids).

Nonlimiting examples include diisopropyl sebacate, diisopropyl adipate, isopropyl myristate, isopropyl palmitate, methyl palmitate, myristyl propionate, 2-ethylhexyl palmitate, isodecyl neopentanoate, di-2-ethylhexyl maleate, cetyl palmitate, myristyl myristate, stearyl stearate, isopropyl isostearate, methyl stearate, cetyl stearate, behenyl behenrate, dioctyl maleate, dioctyl sebacate, diisopropyl adipate, cetyl octanoate, and diisopropyl dilinoleate.

5) mono-. di- and tri- glycerides of $C_1$–$C_{30}$ carboxylic acids

Such thickening agents include caprylic/capric triglyceride, PEG6 caprylic/capric triglyceride, PEG-8 caprylic/capric triglyceride, etc.

6) alkylene glycol esters of $C_1$–$C_{30}$ carboxylic acids

Suitable thickening agents include ethylene glycol mono- and di-esters, and propylene glycol mono- and di-esters of $C_1$–$C_{30}$ carboxylic acids (e.g., ethylene glycol distearate).

7) propoxylated and ethoxylated derivatives of the foregoing materials.

8) $C_1$–$C_{30}$ mono- and poly- esters of sugars and related materials

These esters are derived from a sugar or polyol moiety and one or more carboxylic acid moieties. Depending on the constituent acid and sugar, these esters can be in either liquid or solid form at room temperature. Examples of liquid esters include: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof. Examples of solid esters include: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 2:6 molar ratio; and the octaester of sucrose wherein the esterifying carboxylic acid moieties are laurate, linoleate and behenate in a 1:3:4 molar ratio. A preferred solid material is sucrose polyester in which the degree of esterification is 7–8, and in which the fatty acid moieties are $C_{18}$ mono- and/or di-unsaturated and behenic, in a molar ratio of unsaturates:behenic of 1:7 to 3:5. A particularly preferred solid sugar polyester is the octaester of sucrose in which there are about 7 behenic fatty acid moieties and about 1 oleic acid moiety in the molecule. Other materials include cottonseed oil or soybean oil fatty acid esters of sucrose. The ester materials are further described in, U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977, U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985.

9) Organopolysiloxane oils

The organopolysiloxane oil may be volatile, non-volatile, or a mixture of volatile and non-volatile silicones. The term "nonvolatile" as used in this context refers to those silicones that are liquid under ambient conditions and have a flash point (under one atmospheric of pressure) of or greater than about 100° C. The term "volatile" as used in this context refers to all other silicone oils. Suitable organopolysiloxanes can be selected from a wide variety of silicones spanning a broad range of volatilities and viscosities. Nonvolatile polysiloxanes are preferred. Nonlimiting examples of suitable silicones are disclosed in U.S. Pat. No. 5,069,897, to Orr, issued Dec. 3, 1991. Examples of suitable organopolysiloxane oils include polyalkylsiloxanes, cyclic polyalkylsiloxanes, and polyalkylarylsiloxanes.

Polyalkylsiloxanes useful in the composition herein include polyalkylsiloxanes with viscosities of from about 0.5 to about 1,000,000 centistokes at 25° C. Such polyalkylsiloxanes can be represented by the general chemical formula $R_3SiO[R_2SiO]_xSiR_3$ wherein R is an alkyl group having from one to about 30 carbon atoms (preferably R is methyl or ethyl, more preferably methyl; also mixed alkyl groups can be used in the same molecule), and x is an integer from 0 to about 10,000, chosen to achieve the desired molecular weight which can range to over about 10,000,000. Commercially available polyalkylsiloxanes include the polydimethylsiloxanes, which are also known as dimethicones, examples of which include the Vicasil® series sold by General Electric Company and the Dow Corning® 200 series sold by Dow Corning Corporation. Specific examples of suitable polydimethylsiloxanes include Dow Corning® 200 fluid having a viscosity of 0.65 centistokes and a boiling point of 100° C., Dow Corning® 225 fluid having a viscosity of 10 centistokes and a boiling point greater than 200° C., and Dow Corning® 200 fluids having viscosities of 50, 350, and 12,500 centistokes, respectively, and boiling points greater than 200° C. Suitable dimethicones include those represented by the chemical formula $(CH_3)_3SiO[(CH_3)_2SiO]_x[CH_3RSiO]_ySi(CH_3)_3$ wherein R is straight or branched chain alkyl having from 2 to about 30 carbon atoms and x and y are each integers of 1 or greater selected to achieve the desired molecular weight which can range to over about 10,000,000. Examples of these alkyl-substituted dimethicones include cetyl dimethicone and lauryl dimethicone.

Cyclic polyalkylsiloxanes suitable for use in the composition include those represented by the chemical formula $[SiR_2—O]_n$ wherein R is an alkyl group (preferably R is methyl or ethyl, more preferably methyl) and n is an integer from about 3 to about 8, more preferably n is an integer from about 3 to about 7, and most preferably n is an integer from about 4 to about 6. When R is methyl, these materials are typically referred to as cyclomethicones. Commercially available cyclomethicones include Dow Corning® 244 fluid having a viscosity of 2.5 centistokes, and a boiling point of 172° C., which primarily contains the cyclomethicone tetramer (i.e. n=4), Dow Corning® 344 fluid having a viscosity of 2.5 centistokes and a boiling point of 178° C., which primarily contains the cyclomethicone pentamer (i.e. n=5), Dow Corning® 245 fluid having a viscosity of 4.2 centistokes and a boiling point of 205° C., which primarily contains a mixture of the cyclomethicone tetramer and pentamer (i.e. n=4 and 5), and Dow Corning® 345 fluid having a viscosity of 4.5 centistokes and a boiling point of 217° C., which primarily contains a mixture of the cyclomethicone tetramer, pentamer, and hexamer (i.e. n=4, 5, and 6).

Also useful are materials such as trimethylsiloxysilicate, which is a polymeric material corresponding to the general chemical formula $[(CH_2)_3SiO_{1/2}]_x[SiO_2]y$, wherein x is an integer from about 1 to about 500 and y is an integer from about 1 to about 500. A commercially available trimethylsiloxysilicate is sold as a mixture with dimethicone as Dow Corning® 593 fluid.

Dimethiconols are also suitable for use in the composition. These compounds can be represented by the chemical formulas $R_3SiO[R_2SiO]_xSiR_2OH$ and $HOR_2SiO[R_2SiO]_xSiR_2OH$ wherein R is an alkyl group (preferably R is methyl or ethyl, more preferably methyl) and x is an integer from 0 to about 500, chosen to achieve the desired molecular weight. Commercially available dimethiconols are typically sold as mixtures with dimethicone or cyclomethicone (e.g. Dow Corning® 1401, 1402, and 1403 fluids).

Polyalkylaryl siloxanes are also suitable for use in the composition. Polymethylphenyl siloxanes having viscosities from about 15 to about 65 centistokes at 25° C. are especially useful.

Preferred for use herein are organopolysiloxanes selected from the group consisting of polyalkylsiloxanes, alkyl substituted dimethicones, cyclomethicones, trimethylsiloxysilicates, dimethiconols, polyalkylaryl siloxanes, and mixtures thereof. More preferred for use herein are polyalkylsiloxanes and cyclomethicones. Preferred among the polyalkylsiloxanes are dimethicones.

10) Vegetable oils and hydrogenated vegetable oils

Examples of vegetable oils and hydrogenated vegetable oils include safflower oil, castor oil, coconut oil, cottonseed oil, menhaden oil, palm kernel oil, palm oil, peanut oil, soybean oil, rapeseed oil, linseed oil, rice bran oil, pine oil, sesame oil, sunflower seed oil, hydrogenated safflower oil, hydrogenated castor oil, hydrogenated coconut oil, hydrogenated cottonseed oil, hydrogenated menhaden oil, hydrogenated palm kernel oil, hydrogenated palm oil, hydrogenated peanut oil, hydrogenated soybean oil, hydrogenated rapeseed oil, hydrogenated linseed oil, hydrogenated rice bran oil, hydrogenated sesame oil, hydrogenated sunflower seed oil, and mixtures thereof.

11) Animal fats and oils

Animal fats and oils include, for example, lanolin and derivatives thereof, and cod liver oil.

12) Also useful are C4–C20 alkyl ethers of polypropylene glycols, C1–C20 carboxylic acid esters of polypropylene glycols, and di-C8–C30 alkyl ethers. Nonlimiting examples of these materials include PPG-14 butyl ether, PPG-15 stearyl ether, dioctyl ether, dodecyl octyl ether, and mixtures thereof.

The hydrophobic phase of the present skin care compositions comprise a dermatologically acceptable light emollient. Generally, light emollients have a molecular weight of up to about 300, are easily spread, and are fast absorbing. Such light emollients allow the present compositions to provide skin moisturization benefits while being quickly absorbed into the skin upon topical application. Such compositions preferably contain from about 0.1% to about 20%, more preferably 0.15% to about 10%, and most preferably 0.2% to about 5% of the light emollient. Emollients, in general, tend to lubricate the skin, increase the smoothness and suppleness of the skin, prevent or relieve dryness of the skin, and/or protect the skin. Emollients are typically water-immiscible, oily or waxy materials. A wide variety of suitable emollients are known and may be used herein. Sagarin, *Cosmetics, Science and Technology*, 2nd Edition, Vol. 1, pp. 32–43 (1972), contains numerous examples of materials suitable as emollients. Preferred light emollients include isohexadecane, isododecane, isoeicosane, $C_{9-16}$ isoparaffin, light mineral oil, isopropyl isostearate, methyl isostearate, ethyl isostearate, isononyl isonononoate, octyl palmitate, isopropyl myristate, isopropyl palmitate, diisopropyl sebacate, hexyl laurate, $C_{12-15}$ alcohol benzoate, dioctyl maleate, diisopropyl adipate, $C_{12-15}$ alcohol salicylate, hydrogenated polyisobutene, octyl salicylate, cylomethicone, dimethicone, and mixtures thereof. More preferred light emollients are isohexadecane, isopropyl isostearate, methyl isostearate, ethyl isostearate, isononyl isonononoate, isopropyl myristate, isopropyl palmitate, dimethicone, and mixtures thereof. Most preferred light emollients are isohexadecane, isopropyl isostearate, methyl isostearate, ethyl isostearate, isononyl isonononoate, dimethicone, and mixtures thereof.

B. Hydrophilic Phase

Emulsions of the present invention also comprise a hydrophilic phase which includes water and/or other hydrophilic diluents. Preferred emulsions contain a dermatologically acceptable, hydrophilic diluent. As used herein, "diluent" includes materials in which the other composition components can be dispersed, dissolved, or otherwise incorporated. Nonlimiting examples of hydrophilic diluents are water, organic hydrophilic diluents such as lower monovalent alcohols (e.g., $C_1$–$C_4$) and low molecular weight glycols and polyols, including propylene glycol, polyethylene glycol (e.g., Molecular Weight 200–600 g/mole), polypropylene glycol (e.g., Molecular Weight 425–2025 g/mole), glycerol, butylene glycol, 1,2,4-butanetriol, sorbitol esters, 1,2,6-hexanetriol, ethanol, isopropanol, butanediol, ether propanol, ethoxylated ethers, propoxylated ethers and combinations thereof. Water is a preferred diluent. The composition preferably comprises from about 60% to about 99.99% of the hydrophilic diluent.

The hydrophilic phase can thus comprise water, or a combination of water and one or more water soluble or dispersible ingredients. Hydrophilic phases comprising water are preferred.

C. Emulsifiers

The emulsion contains an emulsifier, generally to help disperse and suspend the discontinuous phase within the continuous phase. A wide variety of such agents can be employed. Known or conventional emulsifiers can be used in the composition, provided that the selected agent is chemically and physically compatible with essential components of the composition, and provides the desired dispersion characteristics.

The present compositions comprise an emulsifier which is preferably hydrophilic. The compositions of the present invention preferably comprise from about 0.1% to about 5%, more preferably from about 0.15% to about 4%, and most preferably 0.2% to about 3% of an emulsifier. Without intending to be limited by theory, it is believed that the emulsifier assists in dispersing hydrophobic materials, e.g., hydrophobic structuring agents, in the hydrophilic phase. The emulsifier, at a minimum, must be hydrophilic enough to disperse in the hydrophilic phase. Preferred emulsifiers are those having an HLB of at least about 6. The exact emulsifier chosen will depend upon the pH of the composition and the other components present.

Preferred emulsifiers are selected from nonionic emulsifiers. Among the nonionic emulsifiers that are useful herein are those that can be broadly defined as condensation products of long chain alcohols, e.g. $C_{8-30}$ alcohols, with sugar or starch polymers, i.e., glycosides. These compounds can be represented by the formula $(S)_n$—O—R wherein S is a sugar moiety such as glucose, fructose, mannose, and galactose; n is an integer of from about 1 to about 1000, and R is a $C_{8-30}$ alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these emulsifiers include those wherein S is a glucose moiety, R is a $C_{8-20}$ alkyl group, and n is an integer of from about 1 to about 9. Commercially available examples of these emulsifiers include decyl polyglucoside (available as APG 325 CS from Henkel) and lauryl polyglucoside (available as APG 600 CS and 625 CS from Henkel).

Other useful nonionic emulsifiers include the condensation products of alkylene oxides with fatty acids (i.e. alkylene oxide esters of fatty acids). These materials have the general formula $RCO(X)_n OH$ wherein R is a $C_{10-30}$ alkyl group, X is —$OCH_2CH_2$— (i.e. derived from ethylene glycol or oxide) or —$OCH_2CHCH_3$— (i.e. derived from propylene glycol or oxide), and n is an integer from about 6 to about 200. Other nonionic emulsifiers are the condensation products of alkylene oxides with 2 moles of fatty acids (i.e. alkylene oxide diesters of fatty acids). These materials have the general formula $RCO(X)_n OOCR$ wherein R is a $C_{10-30}$ alkyl group, X is —$OCH_2CH_2$— (i.e. derived from ethylene glycol or oxide) or —$OCH_2CHCH_3$— (i.e. derived from propylene glycol or oxide), and n is an integer from about 6 to about 100. Other nonionic emulsifiers are the condensation products of alkylene oxides with fatty alcohols (i.e. alkylene oxide ethers of fatty alcohols). These materials have the general formula $R(X)_n OR'$ wherein R is a $C_{10-30}$ alkyl group, X is —$OCH_2CH_2$— (i.e. derived from ethylene glycol or oxide) or —$OCH_2CHCH_3$— (i.e. derived from propylene glycol or oxide), and n is an integer from about 6 to about 100 and R' is H or a $C_{10-30}$ alkyl group. Still other nonionic emulsifiers are the condensation products of alkylene oxides with both fatty acids and fatty alcohols [i.e. wherein the polyalkylene oxide portion is esterified on one end with a fatty acid and etherified (i.e. connected via an ether linkage) on the other end with a fatty alcohol]. These materials have the general formula $RCO(X)_nOR'$ wherein R and R' are $C_{10-30}$ alkyl groups, X is $-OCH_2CH_2$ (i.e. derived from ethylene glycol or oxide) or $-OCH_2CHCH_3-$ (derived from propylene glycol or oxide), and n is an integer from about 6 to about 100. Nonlimiting examples of these alkylene oxide derived nonionic emulsifiers include ceteth-6, ceteth-10, ceteth-20, steareth6, steareth-10, steareth-20, steareth-21, steareth-100, oleth-10, oleth-20, laureth-23, PEG-6 stearate, PEG-10 stearate, PEG-100 stearate, PEG-12 stearate, PEG-20 glyceryl stearate, PEG-40 stearate, PEG-80 glyceryl tallowate, PEG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof.

Still other useful nonionic emulsifiers include polyhydroxy fatty acid amide emulsifiers corresponding to the structural formula:

wherein: $R^1$ is H, $C_1-C_4$ alkyl, 2-hydroxyethyl, 2-hydroxypropyl, preferably $C_1-C_4$ alkyl, more preferably methyl or ethyl, most preferably methyl; $R^2$ is $C_5-C_{31}$ alkyl or alkenyl, preferably $C_7-C_{19}$ alkyl or alkenyl, more preferably $C_9-C_{17}$ alkyl or alkenyl, most preferably $C_{11}-C_{15}$ alkyl or alkenyl; and Z is a polhydroxyhydrocarbyl moiety having a linear hydrocarbyl chain with at least 3 hydroxyls directly connected to the chain, or an alkoxylated derivative (preferably ethoxylated or propoxylated) thereof. Z preferably is a sugar moiety selected from the group consisting of glucose, fructose, maltose, lactose, galactose, mannose, xylose, and mixtures thereof. An especially preferred surfactant corresponding to the above structure is coconut alkyl N-methyl glucoside amide (i.e., wherein the $R^2CO-$ moiety is derived from coconut oil fatty acids). Processes for making compositions containing polyhydroxy fatty acid amides are disclosed, for example, in G.B. Patent Specification 809, 060, published Feb. 18, 1959, by Thomas Hedley & Co., Ltd.; U.S. Pat. No. 2,965,576, to E. R Wilson, issued Dec. 20, 1960; U.S. Pat. No. 2,703,798, to A. M. Schwartz, issued Mar. 8, 1955; and U.S. Pat. No. 1,985,424, to Piggott, issued Dec. 25, 1934.

Preferred among the nonionic emulsifiers are those selected from the group consisting of steareth-21, ceteth-10, ceteth-20, sucrose cocoate, steareth-100, PEG-100 stearate, and mixtures thereof.

Other nonionic emulsifiers suitable for use herein include sugar esters and polyesters, alkoxylated sugar esters and polyesters, $C_{1-30}$ fatty acid esters of $C_{1-30}$ fatty alcohols, alkoxylated derivatives of C1–C30 fatty acid esters of $C_{1-30}$ fatty alcohols, alkoxylated ethers of $C_{1-30}$ fatty alcohols, polyglyceryl esters of $C_{1-30}$ fatty acids, $C_{1-30}$ esters of polyols, $C_{1-30}$ ethers of polyols, alkyl phosphates, polyoxyalkylene fatty ether phosphates, fatty acid amides, acyl lactylates, and mixtures thereof. Nonlimiting examples of these non-silicon-containing emulsifiers include: polyethylene glycol 20 sorbitan monolaurate (Polysorbate 20), polyethylene glycol 5 soya sterol, Ceteareth-20, PPG-2 methyl glucose ether distearate, Polysorbate 80, cetyl phosphate, potassium cetyl phosphate, diethanolamine cetyl phosphate, Polysorbate 60, glyceryl stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, PPG-2 methyl glucose ether distearate, and mixtures thereof.

Other emulsifiers useful herein are fatty acid ester blends based on a mixture of sorbitan or sorbitol fatty acid ester and sucrose fatty acid ester, the fatty acid in each instance being preferably $C_8-C_{24}$, more preferably $C_{10}-C_{20}$. The preferred fatty acid ester emulsifier is a blend of sorbitan or sorbitol $C_{16}-C_{20}$ fatty acid ester with sucrose $C_{10}-C_{16}$ fatty acid ester, especially sorbitan stearate and sucrose cocoate. This is commercially available from ICI under the trade name Arlatone 2121.

The hydrophilic emulsifiers useful herein can alternatively or additionally include any of a wide variety of cationic, anionic, zwitterionic, and amphoteric emulsifiers such as are known in the art. See, e.g., *McCutcheon's Detergents and Emulsifiers*, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973.

Exemplary cationic emulsifiers useful herein include those disclosed in U.S. Pat. No. 5,151,209, to McCall et al., issued Sep. 29, 1992; U.S. Pat. No. 5,151,210, to Steuri et al., issued Sep. 29, 1992; U.S. Pat. No. 5,120,532, to Wells et al., issued Jun. 9, 1992; U.S. Pat. No. 4,387,090, to Bolich, issued Jun. 7, 1983; U.S. Pat. 3,155,591, Hilfer, issued Nov. 3, 1964; U.S. Pat. No. 3,929,678, to Laughlin et al., issued Dec. 30, 1975; U.S. Pat. No. 3,959,461, to Bailey et al., issued May 25, 1976; *McCutcheon's Detergents & Emulsifiers*, (North American edition 1979) M.C. Publishing Co.; and Schwartz, et al., *Surface Active Agents: Their Chemistry and Technology*, New York, Interscience Publishers (1949). The cationic emulsifiers useful herein include cationic ammonium salts such as quaternary ammonium salts, and amino-amides.

A wide variety of anionic emulsifiers are also useful herein. See, e.g., U.S. Pat. No. 3,929,678, to Laughlin et al., issued Dec. 30, 1975. Nonlimiting examples of anionic emulsifiers include the alkoyl isethionates (e.g., $C_{12}-C_{30}$), alkyl and alkyl ether sulfates and salts thereof, alkyl and alkyl ether phosphates and salts thereof, alkyl methyl laurates (e.g., $C_{12}-C_{30}$ and soaps (e.g., alkali metal salts, e.g., sodium or potassium salts)) of fatty acids.

Amphoteric and zwitterionic emulsifiers are also useful herein. Examples of amphoteric and zwitterionic emulsifiers which can be used in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms (preferably $C_8-C_{18}$) and one contains an anionic water solubilizing group, e.g., carboxy, sulfonate, sulfate, phosphate, or phosphonate. Examples are alkyl imino acetates, and iminodialkanoates and aminoalkanoates, imidazolinium and ammonium derivatives. Other suitable amphoteric and zwitterionic emulsifiers are those selected from the group consisting of betaines, sultaines, hydroxysultaines, alkyl sarcosinates (e.g., $C_{12}-C_{30}$), and alkanoyl sarcosinates.

Emulsions of the present invention may also include a silicone containing emulsifier. A wide variety of silicone emulsifiers are useful herein. These silicone emulsifiers are typically organically modified organopolysiloxanes, also known to those skilled in the art as silicone emulsifiers. Useful silicone emulsifiers include dimethicone copolyols.

These materials are polydimethyl siloxanes which have been modified to include polyether side chains such as polyethylene oxide chains, polypropylene oxide chains, mixtures of these chains, and polyether chains containing moieties derived from both ethylene oxide and propylene oxide. Other examples include alkyl-modified dimethicone copolyols, i.e., compounds which contain $C_2$–$C_{30}$ pendant side chains. Still other useful dimethicone copolyols include materials having various cationic, anionic, amphoteric, and zwitterionic pendant moieties.

The dimethicone copolyol emulsifiers useful herein can be described by the following general structure:

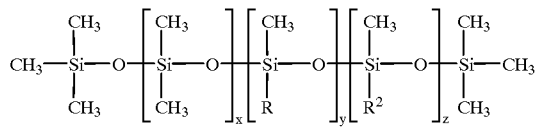

wherein R is $C_{1-30}$ straight, branched, or cyclic alkyl and $R^2$ is selected from the group consisting of

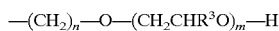

and

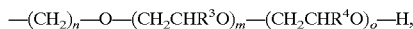

wherein n is an integer from 3 to about 10; $R^3$ and $R^4$ are selected from the group consisting of H and C1–C6 straight or branched chain alkyl such that $R^3$ and $R^4$ are not simultaneously the same; and m, o, x, and y are selected such that the molecule has an overall molecular weight from about 200 to about 10,000,000, with m, o, x, and y being independently selected from integers of zero or greater such that m and o are not both simultaneously zero, and z being independently selected from integers of 1 or greater. It is recognized that positional isomers of these copolyols can be achieved. The chemical representations depicted above for the $R^2$ moieties containing the $R^3$ and $R^4$ groups are not meant to be limiting but are shown as such for convenience.

Also useful herein, although not strictly classified as dimethicone copolyols, are silicone emulsifiers as depicted in the structures in the previous paragraph wherein $R^2$ is:

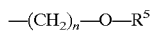

wherein $R^5$ is a cationic, anionic, amphoteric, or zwitterionic moiety.

Nonlimiting examples of dimethicone copolyols and other silicone emulsifiers useful as emulsifiers herein include polydimethylsiloxane polyether copolymers with pendant polyethylene oxide sidechains, polydimethylsiloxane polyether copolymers with pendant polypropylene oxide sidechains, polydimethylsiloxane polyether copolymers with pendant mixed polyethylene oxide and polypropylene oxide sidechains, polydimethylsiloxane polyether copolymers with pendant mixed poly(ethylene)(propylene)oxide sidechains, polydimethylsiloxane polyether copolymers with pendant organobetaine sidechains, polydimethylsiloxane polyether copolymers with pendant carboxylate sidechains, polydimethylsiloxane polyether copolymers with pendant quaternary ammonium sidechains; and also further modifications of the preceding copolymers containing pendant $C_{2-30}$ straight, branched, or cyclic alkyl moieties. Examples of commercially available dimethicone copolyols useful herein sold by Dow Corning Corporation are Dow Corning® 190, 193, Q2-5220, 2501 Wax, 2-5324 fluid, and 3225C (this later material being sold as a mixture with cyclomethicone). Cetyl dimethicone copolyol is commercially available as a mixture with polyglyceryl-4 isostearate (and) hexyl laurate and is sold under the tradename ABIL® WE-09 (available from Goldschmidt). Cetyl dimethicone copolyol is also commercially available as a mixture with hexyl laurate (and) polyglyceryl-3 oleate (and) cetyl dimethicone and is sold under the tradename ABIL® WS-08 (also available from Goldschmidt). Other nonlimiting examples of dimethicone copolyols also include lauryl dimethicone copolyol, dimethicone copolyol acetate, dimethicone copolyol adipate, dimethicone copolyolamine, dimethicone copolyol behenate, dimethicone copolyol butyl ether, dimethicone copolyol hydroxy stearate, dimethicone copolyol isostearate, dimethicone copolyol laurate, dimethicone copolyol methyl ether, dimethicone copolyol phosphate, and dimethicone copolyol stearate. See *International Cosmetic Ingredient Dictionary*. Fifth Edition, 1993.

Dimethicone copolyol emulsifiers useful herein are described, for example, in U.S. Pat. No. 4,960,764, to Figueroa, Jr. et al., issued Oct. 2, 1990; European Patent No. EP 330,369, to SaNogueira, published Aug. 30, 1989; G. H. Dahms, et al., "New Formulation Possibilities Offered by Silicone Copolyols," *Cosmetics & Toiletries*, vol. 110, pp. 91–100, March 1995; M. E. Carlotti et al., "Optimization of W/O-S Emulsions And Study Of The Quantitative Relationships Between Ester Structure And Emulsion Properties," *J. Dispersion Science And Technology*, 13(3), 315–336 (1992); P. Hameyer, "Comparative Technological Investigations of Organic and Organosilicone Emulsifiers in Cosmetic Water-in-Oil Emulsion Preparations," HAPPI 28(4), pp. 88–128 (1991); J. Smid-Korbar et al., "Efficiency and Usability of Silicone Surfactants in Emulsions," *Provisional Communication, International Journal of Cosmetic Science*, 12, 135–139 (1990); and D. G. Krzysik et al., "A New Silicone Emulsifier For Water-in-Oil Systems," *Drug and Cosmetic Industry*, vol. 146(4) pp. 28–81 (April 1990).

Preferred emulsifiers are selected from the group consisting of sorbitan monostearate, sucrose cocoate, steareth-10, steareth-20, steareth-21, steareth-100, oleth-10, oleth-20, laureth-23, cetearyl glucoside, ceteth-10, ceteth-20, PEG-100 stearate, and mixtures thereof.

II. Dispenser

The skin care kit of the present invention comprises a dispenser for the above described skin care composition. This dispenser comprises a manually-operated pump which is fixedly connected to an ergonomic container having an actuator cap. As used herein, "fixedly" means that the pump is not easily removed from the container without destroying the dispenser. "Ergonomic" means the dispenser is shaped so as to provide the user with a comfortable and easy grip. The user's hand should readily conform to the shape of the container and the actuator should be easily depressed substantially solely by movement of the tip of either the thumb or index finger. The dispenser is configured such that the pump is in register with the container. U.S. application Ser. No. 08/784,488, filed Jan. 17, 1997 by Lund et al. further describes an ergonomic package and is incorporated by reference herein in its entirety.

The container can be formed in a wide variety of shapes which include, but are not limited to, substantially cylindrical, oval, elliptical, rectangular, triangular, and combinations thereof. Preferably the container is substantially cylindrical in shape, as shown in the figures contained herein.

Depicted in FIG. 1 is a first embodiment of the invention showing the main components of a dispenser for the present skin care compositions which include a container 2, a headpiece 3 extending therefrom, a closure cap 4 for sealingly closing the dispenser, and a follower piston 5 slidably mounted for displacement within container 2. Headpiece 3 is composed of a body 6 and an actuator cap 7. The individual components of dispenser 1 are made of an injection-moldable plastic, preferably polyethylene, polypropylene, or polyethylene terepthalate, so that dispenser 1 is of a lightweight construction, and the present skin care composition which is filled into container 2 of dispenser 1 is unaffected by the material of dispenser 1. The skin care composition is advanced within container 2 by the displacement of follower piston 5 along the interior wall surface of container 2 by the action thereon of the surrounding atmospheric pressure, so that container 2 is emptied form bottom to top during use of dispenser 1. In this manner the supply of the skin care composition within container 2 towards a dispensing mechanism incorporated in headpiece 3 is ensured in a simple manner, and the generation of a vacuum within container 2 by dispensing the skin care composition from dispenser 1 as well as the entry of outside air to the interior of container is avoided.

Body 6 of headpiece 3 is offset radially inwards of the peripheral wall of container 2 to thereby form a seat for closure cap 4, permitting it to be seated on container 2 in alignment with its peripheral wall surface, so that dispenser 1 as a whole has a smooth outer shape.

Figure 2:
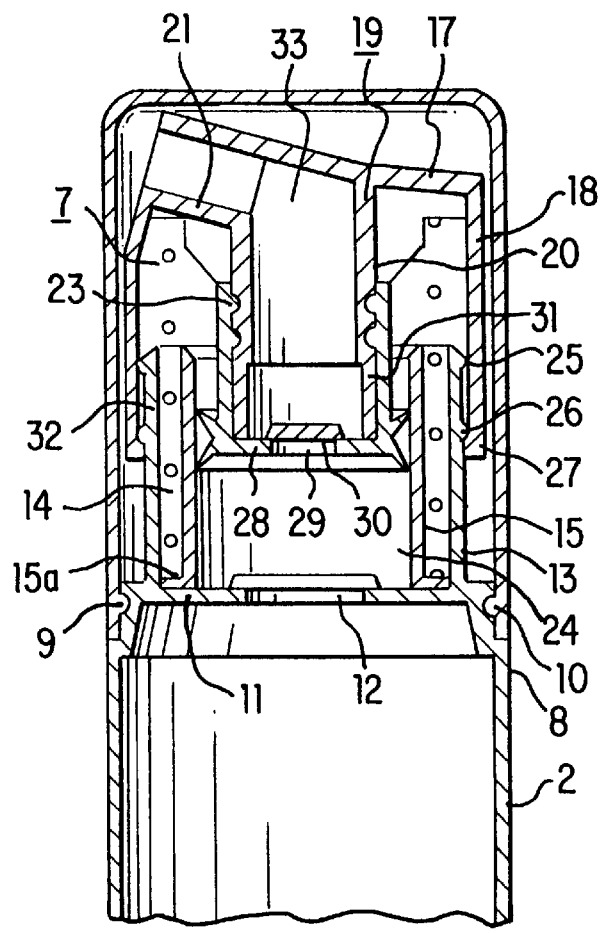
FIG. 2 shows an enlarged illustration of a headpiece of the dispenser shown in FIG. 1.

Details of the first embodiment shall now be explained with reference to FIG. 2, showing an enlarged illustration of headpiece 3 of FIG. 1 including closure cap 4, together with a more detailed illustration of the components of this embodiment.

As shown in FIG. 2, the upper end of container 2 is formed with a shoulder 8 defining a peripheral surface with a detent groove 9 acting as a seat surface for closure cap 4, the latter being formed with an interior annular projection 10 to be received in groove 9 as dispenser 1 is being closed, so that closure cap 4 and container 2 are united with their peripheral wall surfaces in alignment without a gap therebetween. The top end of shoulder 8 is defined by an end wall 11 formed with a central opening 12.

Integrally formed with end wall 11 and extending axially therefrom is an outer sleeve 13 as a basic element of cylinder body 6 forming an axial extension of container 2. The outer diameter of outer sleeve 13 is smaller than that of container 2 to provide sufficient clearance for the sliding displacement of actuator cap 7 and for the application of closure cap 4 in coaxial alignment with container 2. An annular space 14 is defined within outer sleeve 13 by an inner sleeve 15 inserted thereinto with its bottom end resting on end wall 11. The bottom end portion of inner sleeve 15 is formed with a peripheral outer shoulder 15a of a radial width corresponding to that of annular space 14 for centering inner sleeve 15 within outer sleeve 13. Inner sleeve 15 is substantially designed in the shape of a cup, a central bottom portion of which is formed as a closure flap 16 covering opening 12 of end wall 11 and cooperating therewith to form a non-return valve. Closure flap 16 is preferably cut from the bottom portion of inner sleeve 15 along part of its periphery and pivotally connected (i.e., connected such that a joint is formed) to the remainder of said bottom portion by an integral material web. This connection permits closure flap 16 to be pivoted in one direction when a pressure within container 2 adjacent opening 12 exceeds a pressure prevailing above closure flap 16.

Outer sleeve 13 cooperates with inner sleeve 15 to form guide and retention means for actuator cap 7 simultaneously acting as the dispensing mechanism of dispenser 1.

Actuator cap 7 is of a generally cup-shaped configuration comprising a bottom wall 17 and an annular outer wall 18. Within the space defined by bottom wall 17 and outer wall 18 actuator cap 7 is provided with a tubular section 19 itself composed of two distinct portions, namely, an axially extending and centrally located piston carrier tube 20, and a dispensing pipe 21 extending therefrom at an obtuse angle adjacent bottom wall 17 of actuator cap 7. Secured to piston carrier tube 20 is a dispensing piston 22 provided to this purpose with a hollow extension 23 projecting axially into actuator cap 7. The outer diameter of piston 22 is dimensioned so that piston 22 is in sealingly slidable engagement with inner sleeve 15.

Outer sleeve 13 is formed with upper and lower annular projections 25, 26, the peripheral surfaces of which form a guide surface for the interior surface of outer wall 18 of actuator cap 7. A lower end portion of actuator cap 7 is formed with an inwards projecting annular rim 27 cooperating with annular projection 26 of outer sleeve 13 to retain actuator cap 7 on outer sleeve 13 while permitting it to be axially displaced for actuating dispenser 1.

The sealingly slidable engagement of dispenser piston 22 with the interior wall surface of inner sleeve 15 results in the formation of a pump chamber 24 between a bottom portion 28 of dispenser piston 22 and closure flap 16, the volume of pump chamber 24 being variable in response to axial displacement of actuator cap 7 and thus dispensing piston 22. Bottom portion 28 of dispensing piston 22 is formed with an opening 29 covered by a closure flap 30 within piston 22. Closure flap 30 is integrally formed with and pivotally connected to a valve sleeve 31 inserted into dispensing piston 22 and cooperates with opening 29 to form a non-return valve. Valve sleeve 31 is inserted into tubular extension 23 of dispensing piston 22 and has closure flap 30 integrally connected thereto by a web acting as a hinge.

Dispensing piston 22 is secured to piston carrier tube 20 by a snap connection.

Disposed in annular space 14 between inner sleeve 15 and outer sleeve 13 is a helical spring 32 acting as a return spring for actuator cap 7 and held under compression between outer annular shoulder 15a of inner sleeve 15 and bottom wall 17 of actuator cap 7, so that in the absence of an actuating force actuator cap 7 is maintained in the position shown in FIG. 2 and determined by annular projections 26 and 27.

The outer surface of bottom wall 17 of actuator cap 7 forms an actuating surface for the application of an axially downwards directed actuating force for dispensing the skin care composition from dispenser 1 through an outlet passage 33 formed by tubular section 19.

For avoiding a disadvantageous rectangularly bent configuration of outlet passage 33, bottom wall 17 of actuator cap 7 substantially extends in an inclined plane with respect to the longitudinal axis of dispenser 1.

The above described dispenser 1 operates as follows: On the first actuation of dispenser 1, it may be assumed that only container 2 is filled with the skin care composition, so that axial depression of actuator cap 7 initially results in a "dead" stroke of piston 22 to reduce the volume of pump chamber 24. The resultant pressure rise in pump chamber 24 causes closure flap 30 of piston 22 to be lifted off opening 29 in piston bottom portion 28 to thereby permit the air to escape from pump chamber 24 through outlet passage 33. On subsequent release of the actuating force acting on actuator cap 7, return spring 32 acts to return actuator cap 7 upwards to its starting position, whereby the volume of pump chamber 24 is again increased. The resultant vacuum within pump chamber 24 causes closure flap 30 of dispensing piston 22 to return to its rest position obturating opening 29 and closure flap 16 on end wall 11 to be lifted off opening 12 to thereby permit the skin care composition to flow from container 2 into pump chamber 24 until a pressure equilibrium is established between pump chamber 24 and the interior of container 2, whereupon closure flap 16 may close again on opening 12 of end wall 11. Renewed depression of actuator cap 7 on the one hand causes the pressure acting on closure flap 16 to be increased to thereby completely interrupt communication between pump chamber 24 and the interior of container 2, and on the other hand causes closure flap 30 to be lifted off opening 29 in bottom portion 28 of dispensing piston 22, so that the skin care composition is expelled through outlet passage 33, i.e. through piston carrier tube 20 and dispensing pipe 21.

The amount of the skin care composition dispensed is thus determined by the length of the piston stroke expelling the product from pump chamber 24 through outlet passage 33. When the pressure acting on actuator cap 7 is again relieved, return spring 32 again acts to return actuator cap 7 to its rest position, the resultant vacuum in pump chamber 24 causing piston closure flap 30 to be closed, this action being assisted by the amount of the product remaining in outlet passage 33, which tends to be sucked back into pump chamber 24 as long as closure flap 30 has not yet completely closed. At the same time the vacuum generated in pump chamber 24 causes closure flap 16 between the product supply and pump chamber 24 to be opened, so that the skin care composition flows from the interior of container 2 into pump chamber 24 until the latter is again filled with the product and closure flap 16 is permitted to return to its closure position on end wall 11 by the pressure equilibrium thus established.

It is of course also possible to likewise fill pump chamber 24 with the skin care composition prior to the first actuation of dispenser 1, so that the first depression of actuator cap 7 results in the skin care composition to be dispensed from dispenser 1.

The further embodiments of the invention relate to modifications in the design of actuator cap 7 and/or inner and outer sleeves 13 and 15, respectively, without thereby relinquishing the operating principle described above. In all of these embodiments, depression of actuator cap 7 causes the skin care composition to be expelled from pump chamber 24 through outlet passage 33, while the return of actuator cap 7 to its rest position causes a charge of the skin care composition to be sucked into pump chamber 24 from supply container 2. Individual components of the embodiments shown in FIGS. 3 to 7 corresponding to ones of the first embodiment of FIG. 2 are designated by the same reference numerals.

Figure 3:
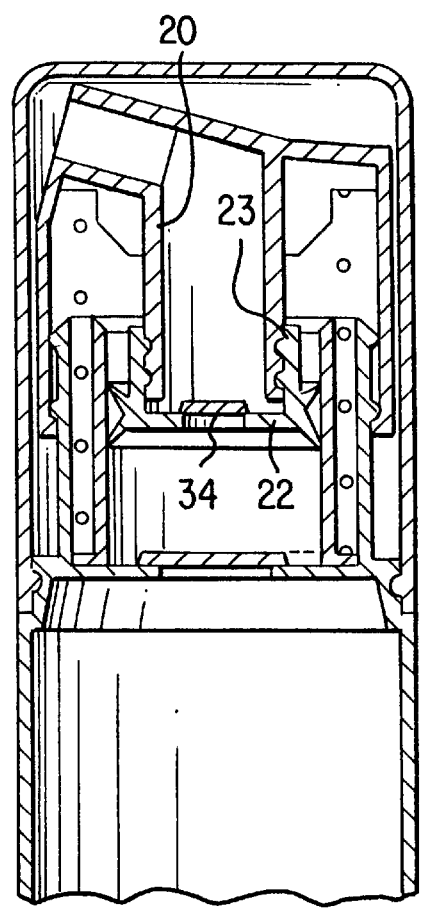
FIG. 3 shows a longitudinal sectional view of a headpiece of a dispenser according to a second embodiment of the invention.

The embodiment of FIG. 3 differs from the one shown in FIG. 2 by the absence of a valve sleeve inserted into dispensing piston 22, in place of which a non-return valve is formed by the cooperation of opening 29 in bottom portion 28 of dispenser piston 22 with a closure member 34 formed integrally with piston carrier tube 20 as a hinged flap projecting at right angles radially inwards. This arrangement results in closure member 34 being reliably biased in the closing direction for obturating opening 29 in bottom wall 28 of dispensing piston 22.

Figure 7:
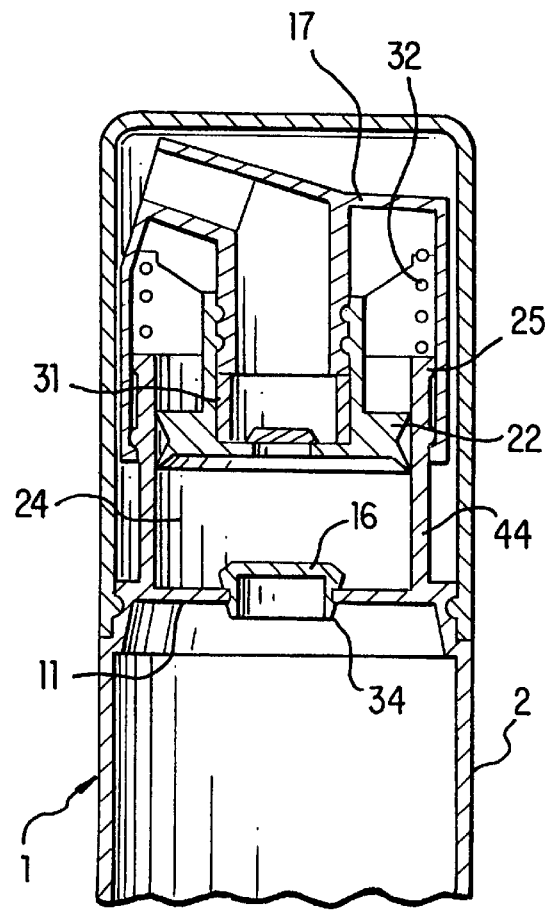
FIG. 7 shows a longitudinal sectional view of the headpiece of a dispenser according to a fifth embodiment of the invention.

Alternatively it is also possible to insert a separate non-return valve similar to the closure of container opening 12 shown in FIG. 7 into opening 29. The omission of valve sleeve 31 permits piston carrier tube 20 to be extended to a location close to the interior surface of piston bottom 28, so that hollow extension 23 of dispenser piston 22 may be made shorter.

Figure 5:
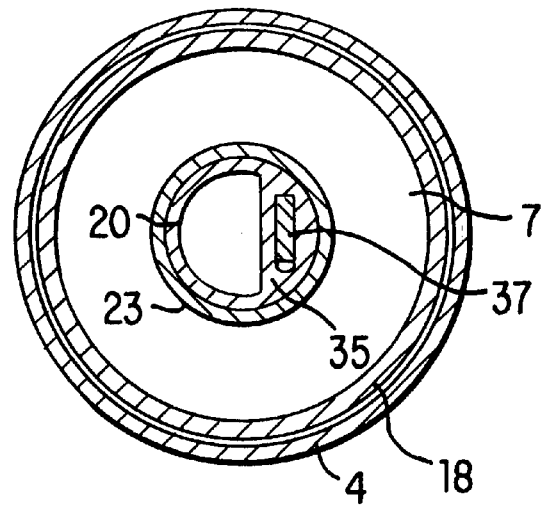
FIG. 5 shows a cross-sectional view taken along the line I—I in FIG. 4.
Figure 4:
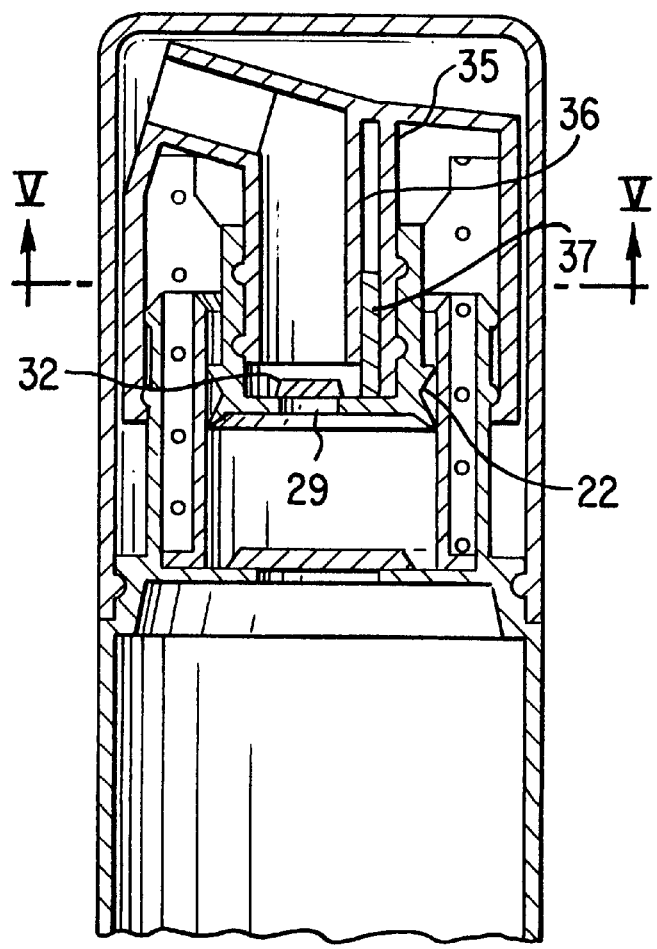
FIG. 4 shows a longitudinal sectional view of a headpiece of a dispenser according to a third embodiment.

A further embodiment shown in FIGS. 4 and 5 differs from the previous ones by a modified mounting of closure flap 32 of the non-return valve in dispensing piston 22. In this embodiment piston carrier tube 20 is formed with a thickened wall segment 35 provided with an axially extending slot 36 for receiving therein a non-circular plastic shaft 37 to which closure flap 32 is pivotally connected by an integrally formed web portion.

This solution ensures a reliable and uncomplicated positioning of closure flap 32 over opening 29 of dispensing piston 22.

Figure 6:
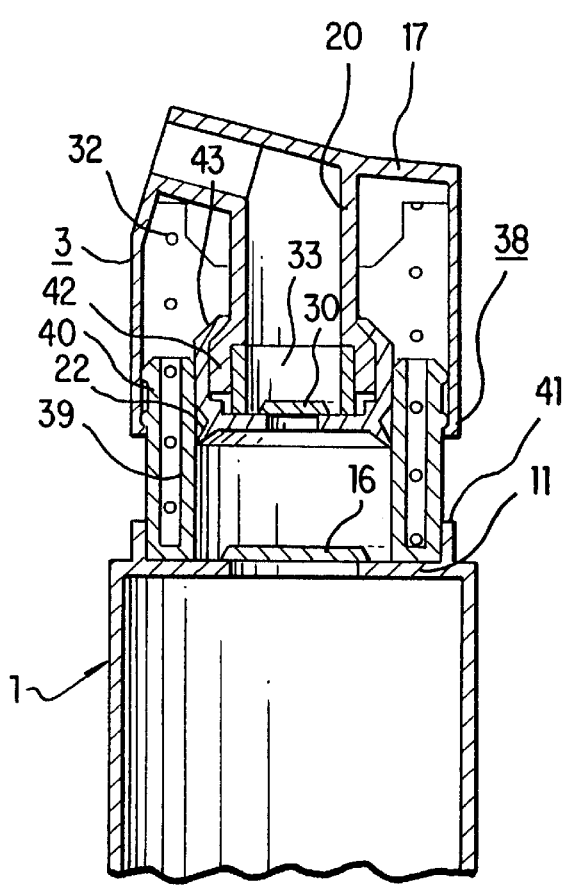
FIG. 6 shows a longitudinal sectional view of a headpiece of a dispenser according to a fourth embodiment of the invention.

FIG. 6 shows an embodiment of dispenser 1 in which a further reduction of the number of components of headpiece 3 is achieved by the provision that, by contrast to the previous embodiments, in which outer and inner sleeves 13 and 15, respectively, are separately formed components, the two sleeves are now combined in an integral component in the form of a cylinder sleeve 38 having a wall of U-shaped cross-sectional configuration comprising an inner wall 39 and an outer wall 40 with a clearance therebetween for accommodating and guiding helical return spring 32 therein. End wall 11 is provided with an integrally formed annular extension 41 in which cylinder sleeve 38 is retained in a press fit.

Also modified with respect to the embodiments shown in FIGS. 1 to 5 is the design of dispensing piston 22 and its mounting on piston carrier tube 20. In the present example the free end of piston carrier tube 20 is formed with an end portion 42 having a larger diameter than the remainder of piston carrier tube 20, so that the circumferential outer surface of piston carrier tube 20 defines an undercut portion 43, while the respective portion of the interior wall surface of piston carrier tube 20 forms a shoulder.

Inserted into enlarged end portion 42 is a valve sleeve 31 similar to the one shown in FIG. 2, serving as a hinged mounting for closure flap 30 of the piston non-return valve and at the same time covering the shoulder inside piston carrier tube 20, so that the flow resistance for the skin care composition is not increased at this location of outlet passage 33.

Dispensing piston 22 is designed in such a manner that hollow extension 23 forms an integral part of the piston sealing surface slidably engaging inner wall 39 of cylinder sleeve 38 together with an upstream sealing lip of dispensing piston 22.

Hollow extension 23 is formed with a restricted annular end portion 44 for snap-engagement with undercut portion 43 defining enlarged end portion 42 of piston carrier tube 20. This arrangement permit dispensing piston 22 to be mounted on piston carrier tube 20 by simply pushing it thereonto, and to be subsequently positively retained thereon, the position of piston 22 in the thus mounted state being defined by valve sleeve 31 or shoulder 42, respectively.

In addition to the simplified mounting in actuator cap 7 of all components required for dispensing the skin care composition, this embodiment offers the advantage of an improved stability and guidance of actuator cap 7 due to the greater dimensions of the piston sealing surface. The outer guidance of actuator cap is achieved independently thereof in a similar manner as in the previous embodiments by the employ of annular projections 25 and 26 formed in this case on outer wall 40 of cylinder sleeve 38.

Closure flap 16 of the non-return valve at the top of container 2 may be formed as a separate closure member or connected by a web portion to inner wall 39 of cylinder sleeve 38.

This embodiment may be further simplified by omitting annular extension 41 for the mounting of cylinder sleeve 38 and by forming the double-walled cylinder sleeve 38 integrally with end wall 11 of container 2.

In this embodiment the handling of dispenser 1 is further facilitated by the provision that the portion of bottom wall 17 of actuator cap 7 receiving the actuating force for operating dispenser 1 is inclined in opposite directions, so that a finger used for actuation is guided to the center of the outer bottom wall surface for uniform application of the actuating force to actuator cap 7.

Also in this embodiment the dispenser operates in the manner described with reference to FIG. 2.

A further simplified construction of the dispensing mechanism of dispenser 1 is shown in FIG. 7. In this case a double-walled construction of cylinder body 3 in the form of separate inner and outer sleeves or in the form of a double-walled sleeve for guiding dispensing piston 22 is omitted, in place of which a single guide sleeve 44 is integrally formed with end wall 11 of container 2, the inner wall surface of guide sleeve 44 serving for slidably guiding piston 22, while its outer wall surface is designed to guide and retain annular wall 18 of actuator cap 7 thereon. The mounting of dispensing piston 22 on piston carrier tube 20 is of the same construction as in FIG. 2. The annular top end face of guide sleeve 44 is of an increased width due to the presence of upper annular projection 25 to act as a support surface for helical spring 32, the other end of which is supported by bottom wall 17 of actuator cap 7. The outer diameter of helical spring 32 is selected so that the interior surface of annular wall 18 of actuator cap 7 acts as a guide for spring 32, the bottom wall of actuator cap 7 being optionally formed with an annular groove for centering spring 32.

This solution characterized not only by the greatest possible simplification of the construction of all components, but also by increasing the volume of pump chamber 24 to a maximum, this volume being of course effective to determine the amount of the product dispensed by a single operation of actuator cap 7. This embodiment of dispenser 1 is thus particularly suited for metering and dispensing relatively greater amounts of the skin care composition.

Apart from the valve components for the two non-return valves, this embodiment of dispenser 1 essentially consists of only three separate components, namely, container 2 with guide sleeve 44, dispensing piston 22, and actuator cap 7, these components being adapted to be readily assembled with helical spring 32 interposed therebetween. At the same time this small number of headpiece components ensures reliable and accurate metering and dispensing of the skin care composition from container 2 through outlet passage 33. The assembly of this dispenser is thus extremely simple, merely requiring the snap-fit mounting of dispensing piston 22 on piston carrier tube 20 with valve sleeve 31 interposed therebetween, and the mounting of actuator cap 7 on guide sleeve 44. Closure flap 16 of the non-return valve at the bottom of pump chamber 24 is preferably formed integrally with and pivotally connected to a sleeve 34 mounted in opening 12 of end wall 11 of container 2 by a simple snap fit mounting. As in this embodiment the volume of pump chamber 24 is substantially increased, the discharge of the correspondingly increased volume of the skin care composition may be expedited by substantially increasing the diameter of piston carrier tube 20 and thus the available volume of outlet passage 33, whereby the construction of dispensing piston 22 is similar to that shown in the other figures.

Dispensing piston 22 may also be formed integrally with piston carrier tube 20, so that its hollow extension 23 can be omitted. In this case closure flap 30 is integrally hinged to bottom portion 28 of dispensing piston 22 at the inner side thereof. Within the basic concept of the invention the dispenser may be further modified, for instance by replacing helical spring 32 with a resilient plastic ring or a similar injection-moulded member of a type similar to the remaining components of dispenser 1. The construction of the non-return valves at the top of container 2 and within dispensing piston 22 may also be modified with a view to the nature and consistency of the skin care composition to be dispensed. The dispenser may be used for any application concerned with the metered dispensing of skin care compositions, such as for medical applications, cosmetic and body care applications.

The present invention results in a skin care product which involves a dispenser comprising a dispensing piston mechanism for extracting and dispensing such compositions from a supply container, without thereby impairing the reliability and metering accuracy of a dispenser of this type. The actuator cap with its dispensing piston combines the metering and dispensing functions with the actuating function of the dispenser, resulting in a simple and compact construction of the headpiece of the dispenser in combination with a simplification of the construction of individual components and a reduction of their number. Suitable dispensers are further described in U.S. Pat. No. 4,875,604, issued to Czech, on Oct. 24, 1989, which is incorporated herein by reference in its entirety.

A preferred embodiment of the present invention comprises a skin care composition contained in a dispenser such that the composition comprises an oil-in-water emulsion, a polymeric thickening agent, a reflective particulate material selected from the group consisting of $TiO_2$, ZnO, $ZrO_2$, and mixtures thereof, such that the composition has a viscosity of from about 20,000 to about 100,000 and a pH of from about 4 to about 8. In another preferred embodiment, the light emollient is selected from the group consisting of isohexadecane, isopropyl isostearate, methyl isostearate, ethyl isostearate, isononyl isonononoate, dimethicone, and mixtures thereof; the emulsifier of the skin care composition is selected from the group consisting of sorbitan monostearate, sucrose cocoate, steareth-10, steareth-20, steareth-21, steareth-100, oleth-10, oleth-20, laureth-23, cetearyl glucoside, ceteth-10, ceteth-20, PEG-100 stearate, and mixtures thereof; and the composition further comprises niacinamide (a skin care active).

In another preferred embodiment, the present skin care kit comprises a skin care composition contained within a dispenser and the composition comprises an emulsion comprising at least one hydrophobic phase with a light emollient, at least one hydrophilic phase, an emulsifier having an HLB of at least 6, a reflective particulate material, and a vitamin $B_3$ compound such that the composition has a viscosity of about 15,000 cps to about 200,000 cps and a pH of about 3 to about 9. Furthermore, the dispenser comprises an manually-operated pump fixedly connected to an ergonomic container having an actuator cap such that the dispenser is configured so that the pump is in register with the container and the container is shaped so as to provide for comfortable and easy gripping by a human hand. The hand should readily conform to the shape of the container and the actuator can be depressed substantially solely by movement of the tip of either the thumb or index finger. In another embodiment, the skin care composition comprises an oil-in-water emulsion with at least one hydrophobic phase having an oil and a light emollient selected from the group consisting of isohexadecane, isopropyl isostearate, methyl isostearate, ethyl isostearate, isononyl isonononoate, dimethicone, an mixtures thereof; at least one hydrophilic phase comprising water, and an emulsifier selected from the group consisting of sorbitan monostearate, sucrose cocoate, steareth-10, steareth-20, steareth-21, steareth-100, oleth-10, oleth-20, laureth-23, cetearyl glucoside, ceteth-10, ceteth-20, PEG-100 stearate, and mixtures thereof; a polymeric thickening agent; a reflective particulate material selected from the group consisting of $TiO_2$, $ZnO$, $ZrO_2$, and mixtures thereof; and niacinamide; wherein the composition has a viscosity of from about 25,000 cps to about 60,000 cps and a pH of from about 5 to about 7.

III. Optional Components

The skin care compositions of the present invention may comprise a wide variety of optional components, provided that such optional components are physically and chemically compatible with the essential components described herein, and do not unduly impair stability, efficacy or other use benefits associated with the compositions of the present invention. Optional components may be dispersed, dissolved or the like in the carrier of the present compositions.

Optional components include aesthetic agents and active agents. For example, the compositions may include, in addition to the essential components of the invention, absorbents (including oil absorbents such as clays an polymeric absorbents), abrasives, anticaking agents, antifoaming agents, antimicrobial agents (e.g., a compound capable of destroying microbes, preventing the development of microbes or preventing the pathogenic action of microbes and useful, for example, in controlling acne and/or preserving the topical composition), binders, biological additives, buffering agents, bulking agents, chemical additives, cosmetic biocides, denaturants, cosmetic astringents, drug astringents, external analgesics, film formers, humectants, opacifying agents, fragrances, perfumes, pigments, colorings, essential oils, skin sensates, emollients, skin soothing agents, skin healing agents, pH adjusters, plasticizers, preservatives, preservative enhancers, propellants, reducing agents, skin-conditioning agents, skin penetration enhancing agents, skin protectants, solvents, suspending agents, emulsifiers, thickening agents, solubilizing agents, polymers for aiding the film-forming properties and substantivity of the composition (such as a copolymer of eicosene and vinyl pyrrolidone, an example of which is available from GAF Chemical Corporation as Ganex® V-220), waxes, sunscreens, sunblocks, ultraviolet light absorbers or scattering agents, sunless tanning agents, antioxidants and/or radical scavengers, chelating agents, sequestrants, anti-acne agents, anti-inflammatory agents, anti-androgens, depilation agents, desquamation agents/exfoliants, organic hydroxy acids, vitamins and derivatives thereof (including water dispersible or soluble vitamins such as Vitamin C and ascorbyl phosphates), compounds which stimulate collagen production, and natural extracts. Such other materials are known in the art. Nonexclusive examples of such materials are described in *Harry's Cosmeticology*, 7th Ed., Harry & Wilkinson (Hill Publishers, London 1982); in *Pharmaceutical Dosage Forms - Disperse Systems*; Lieberman, Rieger & Banker, Vols. 1 (1988) & 2 (1989); Marcel Decker, Inc.; in *The Chemistry and Manufacture of Cosmetics*, 2nd. Ed., deNavarre (Van Nostrand 1962–1965); and in *The Handbook of Cosmetic Science and Technology*, 1st Ed., Knowlton & Pearce (Elsevier 1993) can also be used in the present invention.

A. Thickening Agent (including thickeners and gelling agents)

The compositions of the present invention can also comprise a thickening agent, preferably from about 0.1% to about 5%, more preferably from about 0.15% to about 4%, and most preferably from about 0.2% to about 3%, of a thickening agent.

Nonlimiting classes of thickening agents include those selected from the group consisting of:

1) Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. The preferred carboxylic acid polymers are of two general types. The first type of polymer is a crosslinked homopolymer of an acrylic acid monomer or derivative thereof (e.g., wherein the acrylic acid has substituents on the two and three carbon positions independently selected from the group consisting of $C_{1-4}$ alkyl, —CN, —COOH, and mixtures thereof). The second type of polymer is a crosslinked copolymer having a first monomer selected from the group consisting of an acrylic acid monomer or derivative thereof (as just described in the previous sentence), a short chain alcohol (i.e., a $C_{1-4}$) acrylate ester monomer or derivative thereof (e.g., wherein the acrylic acid portion of the ester has substituents on the two and three carbon positions independently selected from the group consisting of $C_{1-4}$ alkyl, —CN, —COOH, and mixtures thereof), and mixtures thereof; and a second monomer which is a long chain alcohol (i.e. $C_{8-40}$) acrylate ester monomer or derivative thereof (e.g., wherein the acrylic acid portion of the ester has substituents on the two and three carbon positions independently selected from the group consisting of $C_{1-4}$ alkyl, —CN, —COOH, and mixtures thereof). Combinations of these two types of polymers are also useful herein.

In the first type of crosslinked homopolymers, the monomers are preferably selected from the group consisting of acrylic acid, methacrylic acid, ethacrylic acid, and mixtures thereof with acrylic acid being most preferred. In the second type of crosslinked copolymers the acrylic acid monomer or derivative thereof is preferably selected from the group consisting of acrylic acid, methacrylic acid, ethacrylic acid, and mixtures thereof, with acrylic acid, methacrylic acid, and mixtures thereof being most preferred. The short chain alcohol acrylate ester monomer or derivative thereof is preferably selected from the group consisting of $C_{1-4}$ alcohol acrylate esters, $C_{1-4}$ alcohol methacrylate esters, $C_{1-4}$ alcohol ethacrylate esters, and mixtures thereof, with the $C_{1-4}$ alcohol acrylate esters, $C_{1-4}$ alcohol methacrylate esters, and mixtures thereof, being most preferred. The long chain alcohol acrylate ester monomer is selected from $C_{8-40}$ alkyl acrylate esters, with $C_{10-30}$ alkyl acrylate esters being preferred.

The crosslinking agent in both of these types of polymers is a polyalkenyl polyether of a polyhydric alcohol containing more than one alkenyl ether group per molecule, wherein the parent polyhydric alcohol contains at least 3 carbon atoms and at least 3 hydroxyl groups. Preferred crosslinkers are those selected from the group consisting of allyl ethers of sucrose and allyl ethers of pentaerythritol, and mixtures thereof. These polymers useful in the present invention are more fully described in U.S. Pat. No. 5,087,445, to Haffey et al., issued Feb. 11, 1992; U.S. Pat. No. 4,509,949, to Huang et al., issued Apr. 5, 1985; U.S. Pat. No. 2,798,053, to Brown, issued Jul. 2, 1957. See also, *CTFA International Cosmetic Ingredient Dictionary*, fourth edition, 1991, pp. 12 and 80.

Examples of commercially available homopolymers of the first type useful herein include the carbomers, which are homopolymers of acrylic acid crosslinked with allyl ethers of sucrose or pentaerytritol. The carbomers are available as the Carbopol® 900 series from B.F. Goodrich (e.g., Carbopol® 954). Examples of commercially available copolymers of the second type useful herein include copolymers of $C_{10-30}$ alkyl acrylates with one or more monomers of acrylic acid, methacrylic acid, or one of their short chain (i.e. $C_{1-4}$ alcohol) esters, wherein the crosslinking agent is an allyl ether of sucrose or pentaerytritol. These copolymers are known as acrylates/C10–30 alkyl acrylate crosspolymers and are commercially available as Carbopol® 1342, Carbopol® 1382, Pemulen TR-1, and Pemulen TR-2, from B.F. Goodrich. In other words, examples of carboxylic acid polymer thickeners useful herein are those selected from the group consisting of carbomers, acrylates/$C_{10}$–$C_{30}$ alkyl acrylate crosspolymers, and mixtures thereof.

2) Crosslinked Polyacrylate Polymers

The crosslinked polyacrylate polymers useful as thickeners or gelling agents include both cationic and nonionic polymers, with the cationics being generally preferred. Examples of useful crosslinked nonionic polyacrylate polymers and crosslinked cationic polyacrylate polymers are those described in U.S. Pat. 5,100,660, to Hawe et al., issued Mar. 31, 1992; U.S. Pat. 4,849,484, to Heard, issued Jul. 18, 1989; U.S. Pat. 4,835,206, to Farrar et al., issued May 30, 1989; U.S. Pat. 4,628,078 to Glover et al. issued Dec. 9, 1986; U.S. Pat. 4,599,379 to Flesher et al. issued Jul. 8, 1986; and EP 228,868, to Farrar et al., published Jul. 15, 1987.

The crosslinked polyacrylate polymers are high molecular weight materials that can be characterized by the general formula: $(A)_l(B)_m(C)_n$ and comprise the monomer units $(A)_l$, $(B)_m$, and $(C)_n$, wherein (A) is a dialkylaminoalkyl acrylate monomer or its quaternary ammonium or acid addition salt, (B) is a dialkylaminoalkyl methacrylate monomer or its quaternary ammonium or acid addition salt, (C) is a monomer that is polymerizable with (A) or (B), for example a monomer having a carbon-carbon double bond or other such polymerizable functional group, l is an integer of 0 or greater, m is an integer of 0 or greater, n is an integer of 0 or greater, but where either l or m, or both, must be 1 or greater.

The (C) monomer can be selected from any of the commonly used monomers. Nonlimiting examples of these monomers include ethylene, propylene, butylene, isobutylene, eicosene, maleic anhydride, acrylamide, methacrylamide, maleic acid, acrolein, cyclohexene, ethyl vinyl ether, and methyl vinyl ether. In the cationic polymers of the present invention, (C) is preferably acrylamide. The alkyl portions of the (A) and (B) monomers are short chain length alkyls such as $C_1$–$C_8$, preferably $C_1$–$C_5$, more preferably $C_1$–$C_3$, and most preferably $C_1$–$C_2$. When quaternized, the polymers are preferably quaternized with short chain alkyls, i.e., $C_1$–$C_8$, preferably $C_1$–$C_5$, more preferably $C_1$–$C_3$, and most preferably $C_1$–$C_2$. The acid addition salts refer to polymers having protonated amino groups. Acid addition salts can be performed through the use of halogen (e.g. chloride), acetic, phosphoric, nitric, citric, or other acids.

These $(A)_l(B)_m(C)_n$ polymers also comprise a crosslinking agent, which is most typically a material containing two or more unsaturated functional groups. The crosslinking agent is reacted with the monomer units of the polymer and is incorporated into the polymer thereby forming links or covalent bonds between two or more individual polymer chains or between two or more sections of the same polymer chain. Nonlimiting examples of suitable crosslinking agents include those selected from the group consisting of methylenebisacrylamides, diallyldialkyl ammonium halides, polyalkenyl polyethers of polyhydric alcohols, allyl acrylates, vinyloxyalkylacrylates, and polyfunctional vinylidenes. Specific examples of crosslinking agents useful herein include those selected from the group consisting of methylenebisacrylamide, ethylene glycol di-(meth)acrylate, di-(meth)acrylamide, cyanomethylacrylate, vinyloxyethylacrylate, vinyloxyethylmethacrylate, allyl pentaerythritol, trimethylolpropane diallylether, allyl sucrose, butadiene, isoprene, divinyl benzene, divinyl naphthalene, ethyl vinyl ether, methyl vinyl ether, and allyl acrylate. Other crosslinkers include formaldehyde and glyoxal. Preferred for use herein as a crosslinking agent is methylenebisacrylamide.

Widely varying amounts of the crosslinking agent can be employed depending upon the properties desired in the final polymer, e.g. viscosifying effect. Without being limited by theory, it is believed that incorporation of a crosslinking agent into these cationic polymers provides a material that is a more effective viscosifying agent without negatives such as stringiness and viscosity breakdown in the presence of electrolytes. The crosslinking agent, when present, can comprise from about 1 ppm to about 1000 ppm, preferably from about 5 ppm to about 750 ppm, more preferably from about 25 ppm to about 500 ppm, even more preferably from about 100 ppm to about 500 ppm, and most preferably from about 250 ppm to about 500 ppm of the total weight of the polymer on a weight/weight basis.

The intrinsic viscosity of the crosslinked polymer, measured in one molar sodium chloride solution at 25° C., is generally above 6, preferably from about 8 to about 14. The molecular weight (weight average) of the crosslinked polymers hereof is high, and is believed to typically be between about 1 million and about 30 million. The specific molecular weight is not critical and lower or higher weight average molecular weights can be used as long as the polymer retains its intended viscosifying effects. Preferably, a 1.0% solution of the polymer (on an actives basis) in deionized water will have a viscosity at 25° C. of at least about 20,000 cP, preferably at least about 30,000 cP, when measured at 20 RPM by a Brookfield RVT (Brookfield Engineering Laboratories, Inc. Stoughton, Mass., USA).

These cationic polymers can be made by polymerization of an aqueous solution containing from about 20% to about 60%, generally from about 25% to about 40%, by weight monomer, in the presence of an initiator (usually redox or thermal) until the polymerization terminates. The crosslinking agent can also be added to the solution of the monomers to be polymerized, to incorporate it into the polymer. In the polymerization reactions, the temperature generally starts between about 0° and 95° C. The polymerization can be conducted by forming a reverse phase dispersion of an aqueous phase of the monomers (and also any additional crosslinking agents) into a nonaqueous liquid, e.g. mineral oil, lanolin, isododecane, oleyl alcohol, and other volatile and nonvolatile esters, ethers, and alcohols, and the like.

All percentages describing the polymer in this section of the description herein are molar, unless otherwise specified. When the polymer contains (C) monomer, the molar proportion of (C) monomer, based on the total molar amount of (A), (B), and (C), can be from 0% to about 99%. The molar proportions of (A) and (B) can each be from 0% to 100%. When acrylamide, is used as the (C) monomer, it will preferably be used at a level of from about 20% to about 99%, more preferably from about 50% to about 90%.

Where monomer (A) and (B) are both present, the ratio of monomer (A) to monomer (B) in the final polymer, on a molar basis, is preferably from about 99:5 to about 15:85, more preferably from about 80:20 to about 20:80. Alternatively, in another class of polymers, the ratio is from about 5:95 to about 50:50, preferably from about 5:95 to about 25:75.

In another alternative class of polymers, the ratio (A):(B) is from about 50:50 to about 85:15. Preferably the ratio (A):(B) is about 60:40 to about 85:15, most preferably about 75:25 to about 85:15.

Most preferred is where monomer (A) is not present and the ratio of monomer (B):monomer (C) is from about 30:70 to about 70:30, preferably from about 40:60 to about 60:40 and most preferably from about 45:55 to about 55:45.

Cationic polymers that are useful herein that are especially preferred are those conforming to the general structure $(A)_l B)_m (C)_n$ wherein l is zero, (B) is methyl quaternized dimethylaminoethyl methacrylate, the ratio of (B):(C) is from about 45:55 to about 55:45, and the crosslinking agent is methylenebisacrylamide. An example of such a cationic polymer is one that is commercially available as a mineral oil dispersion (which can also include various dispersing aids such as PPG-1 trideceth-6) under the trademark Salcare® SC92 from Allied Colloids Ltd. (Norfolk, Va.). This polymer has the proposed CTFA designation, "Polyquaternium 32 (and) Mineral Oil".

Other cationic polymers useful herein, are those not containing acrylamide or other (C) monomers, that is, n is zero. In these polymers the (A) and (B) monomer components are as described above. An especially preferred group of these non-acrylamide containing polymers is one in which l is also zero. In this instance the polymer is essentially a homopolymer of a dialkylaminoalkyl methacrlyate monomer or its quaternary ammonium or acid addition salt. These diaklylaminoalkyl methacrylate polymers preferably contain a crosslinking agent as described above.

A cationic polymer, which is essentially a homopolymer, useful herein is one conforming to the general structure $(A)_l(B)_m(C)_n$ wherein l is zero, (B) is methyl quaternized dimethylaminoethyl methacrylate, n is zero, and the crosslinking agent is methylenebisacrylamide. An example of such a homopolymer is commercially available as a mixture containing approximately 50% of the polymer, approximately 44% mineral oil, and approximately 6% PPG-1 trideceth-6 as a dispersing aid, from Allied Colloids Ltd, (Norfolk, Va.) under the trademark Salcare® SC95. This polymer has recently been given the CTFA designation "Polyquaternium 37 (and) Mineral Oil (and) PPG-1 Trideceth-6".

3) Polyacrylamide Polymers

Also useful herein are polyacrylamide polymers, especially non-ionic polyacrylamide polymers including substituted branched or unbranched polymers. These polymers can be formed from a variety of monomers including acrylamide and methacrylamide which are unsubstituted or substituted with one or two alkyl groups (preferably $C_1$ to $C_5$). Preferred are acrylate amide and methacrylate amide monomers in which the amide nitrogen is unsubstituted, or substituted with one or two $C_1$ to $C_5$ alkyl groups (preferably methyl, ethyl, or propyl), for example, acrylamide, methacrylamide, N-methacrylamide, N-methylmethacrylamide, N,N-dimethylmethacrylamide, N-isopropylacrylamide, N-isopropylmethacrylamide, and N,N-dimethylacrylamide. These polymers have a molecular weight greater than about 1,000,000 preferably greater than about 1,5000,000 and range up to about 30,000,000. Most preferred among these polyacrylamide polymers is the non-ionic polymer given the CTFA designation polyacrylamide and isoparaffin and laureth-7, available under the Tradename Sepigel 305 from Seppic Corporation (Fairfield, N.J.).

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc., (Patterson, N.J.).

4) Polysaccharides

A wide variety of polysaccharides are useful herein. By "polysaccharides" are meant gelling agents containing a backbone of repeating sugar (i.e. carbohydrate) units. Nonlimiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl substituted celluloses. In these polymers, the hydroxy groups of the cellulose polymer is hydroxyalkylated (preferably hydroxyethylated or hydroxypropylated) to form a hydroxyalkylated cellulose which is then further modified with a C10–C30 straight chain or branched chain alkyl group through an ether linkage. Typically these polymers are ethers of C10–C30 straight or branched chain alcohols with hydroxyalkylcelluloses. Examples of alkyl groups useful herein include those selected from the group consisting of stearyl, isostearyl, lauryl, myristyl, cetyl, isocetyl, cocoyl (i.e. alkyl groups derived from the alcohols of coconut oil), palmityl, oleyl, linoleyl, linolenyl, ricinoleyl, behenyl, and mixtures thereof. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Other useful polysaccharides include scleroglucans comprising a linear chain of (1–>3) linked glucose units with a (1–>6) linked glucose every three units, a commercially available example of which is Clearogel™ CS11 from Michel Mercier Products Inc. (Mountainside, N.J.).

5) Gums

Other additional thickening and gelling agents useful herein include materials which are primarily derived from natural sources. Nonlimiting examples of these gelling agent gums include materials selected from the group consisting of acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

6) Crosslinked Vinyl Ether/Maleic Anhydride Copolymers

Other additional thickening and gelling agents useful herein include crosslinked copolymers of alkyl vinyl ethers and maleic anhydride. In these copolymers the vinyl ethers are represented by the formula $R-O-CH=CH_2$ wherein R is a C1–C6 alkyl group, preferably R is methyl. Preferred crosslinking agents are C4–C20 dienes, preferably C6 to C16 dienes, and most preferably C8 to C12 dienes. A particularly preferred copolymer is one formed from methyl vinyl ether and maleic anhydride wherein the copolymer has been crosslinked with decadiene, and wherein the polymer when diluted as a 0.5% aqueous solution at pH 7 at 25° C. has a viscosity of 50,000–70,000 cps when measured using a Brookfield RTV viscometer, spindle #7 at 10 rpm. This copolymer has the CTFA designation PVM/MA decadiene crosspolymer and is commercially available as Stabileze™ 06 from International Specialty Products (Wayne, N.J.).

7) Crosslinked poly(N-vinylpyrrolidones)

Crosslinked polyvinyl(N-pyrrolidones) useful herein as additional thickening and gelling agents and include those described in U.S. Pat. No. 5,139,770, to Shih et al, issued Aug. 18, 1992, and U.S. Pat. No. 5,073,614, to Shih et al., issued Dec. 17, 1991, both patents of which are incorporated by reference herein in their entirety. These gelling agents typically contain from about 0.25% to about 1% by weight of a crosslinking agent selected from the group consisting of divinyl ethers and diallyl ethers of terminal diols containing from about 2 to about 12 carbon atoms, divinyl ethers and diallyl ethers of polyethylene glycols containing from about 2 to about 600 units, dienes having from about 6 to about 20 carbon atoms, divinyl benzene, vinyl and allyl ethers of pentaerythritol, and the like. Typically, these gelling agents have a viscosity from about 25,000 cps to about 40,000 cps when measured as a 5% aqueous solution at 25° C. using a Brookfield RVT viscometer with Spindle #6 at 10 rpm. Commercially available examples of these polymers include ACP-1120, ACP-1179, and ACP-1180, available from International Specialty Products (Wayne, N.J.).

Thickening agents which are suitable for use herein also include those disclosed in U.S. Pat. No. , 4,387,107, to Klein et al., issued Jun. 7, 1983 and "Encyclopedia of Polymer and Thickeners for Cosmetics," R. Y. Lochhead and W. R. Fron, eds., *Cosmetics & Toiletries*, vol. 108, pp. 95–135 (May 1993).

Preferred compositions of the present invention include a thickening agent selected from the group consisting of carboxylic acid polymers, crosslinked polyacrylate polymers, polyacrylamide polymers, and mixtures thereof, more preferably selected from the group consisting of crosslinked polyacrylate polymers, polyacrylamide polymers, and mixtures thereof.

B. Reflective Particulate Material

The compositions of the present invention can optionally comprise from about 0.1% to about 2%, preferably from about 0.15% to about 1.5%, more preferably from about 0.2% to about 1%, by weight of the composition, of a reflective particulate material dispersed throughout the hydrophilic phase of the emulsion. These materials provide a visible improvement in skin condition essentially immediately following application of the composition to the skin. Such immediate improvement involves coverage or masking of skin imperfections such as text discontinuities (including those associated with skin aging, such as enlarged pores), and/or providing a more even skin tone or color.

Preferred metallic oxides include $TiO_2$, ZnO, $ZrO_2$ and combinations thereof, more preferably $TiO_2$, ZnO and combinations thereof (combinations are intended to include particles which comprise one or more of these materials, as well as mixtures of these reflective particulate materials). The reflective particulate material may be a composite, e.g., deposited on a core or mixed with other materials such as but not limited to silica, silicone, mica, nylon and polyacrylates, provided that the material has the aforementioned refractive index. The reflective particulate material preferably consists essentially of $TiO_2$, ZnO, $ZrO_2$ or a combination thereof, more preferably $TiO_2$, ZnO or a combination thereof, most preferably, the particles consist essentially of $TiO_2$.

Preferred reflective particulate materials are pigmentary grade. Preferred reflective particulate materials have a primary particle size of from about 100 nm to about 300 nm, more preferably greater than 100 to about 300 nm, even more preferably from about 150 nm to about 300 nm, most preferably from about 200 nm to about 250 mn (e.g., about 220 nm to about 240 nm), in the neat form (i.e., in the essentially pure, powder form prior to combination with any carrier). Preferred reflective particulate materials have an primary particle size when dispersed in the composition of from about 100 nm to about 1000 nm, more preferably from about 100 nm to about 400 nm, even more preferably from about 200 nm to about 300 nm. Primary particle size can be determined using the ASTM Designation E20-85 "Standard Practice for Particle Size Analysis of Particulate Substances in the Range of 0.2 to 75 Micrometers by Optical Microscopy," ASTM Volume 14.02, 1993.

The particles may have a variety of shapes, including spherical, spheroidal, elliptical, lamellar, irregular, needle and rod-like, provided that the desired refractive index is provided. The particulate can be in a variety of physical forms, including rutile, anatase or a combination thereof.

The reflective particulate material can be water-dispersible, oil-dispersible, or a combination thereof. Water- or oil- dispersibility may be inherent to the particle or may be imparted by coating the particles with material to impart a hydrophilic or hydrophobic surface property to the particles. For example, hydrophilic coatings may comprise an amino acid, aluminum oxide or aluminum silicate. Exemplary hydrophobic coatings may comprise organosilicone compounds or metal soaps such as aluminum stearate, aluminum laurate, and zinc stearate. Additonally, a charged coating can be added to prevent agglomeration. Preferred compositions comprise a reflective particulate material comprising a metallic oxide which is coated with a coating material that confers a net charge that is greater than the zeta potential of the uncoated reflective particulate material. Typically, the coating material confers a zeta potential that is greater than about ±20 mV (e.g., either in the positive or negative direction) at pH from about 4 to about 8.5. This provides formulation stability and prevents agglomeration of the reflective particulate materials. Particulates and their charges are well known to those of ordinary skill in the art, and are well described in R. J. Hunter, *Zeta Potential in Colloid Science: Principles and Application* (1981), published by Academic Press; J. N. Israelachvili, *Intermolecular and Surface Forces: With Applications to Colloidal and Biological Systems* (1985), published by Academic Press; and Hoogeven, N.G. et al., *Colloids and Surfaces*, Physiochemical and Engineering Aspects, Vol. 117, p. 77 (1966).

Suitable coating materials which confer a cationic charge include cationic polymers (natural and/or synthetic) and cationic surfactants. Preferred cationic coating materials are selected from the group consisting of chitosan, hydroxypropyl chitosan, quaternium-80, polyquaternium-7, and mixtures thereof.

Nonlimiting examples of coating materials that confer an anionic charge include anionic polymers (natural and/or synthetic) and anionic surfactants. Preferred anionic coating materials are selected from the group consisting of ammonium polyacrylate, sodium polyacrylate, potassium polyacrylate, ethylene acrylic acid copolymer, hydrolyzed wheat protein polysiloxane copolymer, dimethicone copolyol phosphate, dimethicone copolyol acetate, dimethicone copolyol laurate, dimethicone copolyol stearate, dimethicone copolyol behenate, dimethicone copolyol isostearate, dimethicone copolyol hydroxystearate, phosphate ester, sodium chondroiton sulfate, sodium hyaluronate, ammonium hyaluronate, sodium algenate, ammonium algenate, ammonium laurate, sodium laurate, potassium laurate, ammonium myristate, sodium myristate, potassium myristate, ammonium palmitate, sodium palmitate, potassium palmitate, ammonium stearate, sodium stearate, potassium stearate, ammonium oleate, sodium oleate, potassium oleate, and mixtures thereof. More preferred are anionic coating materials selected from the group consisting of ammonium polyacrylate, sodium polyacrylate, and mixtures thereof.

Inorganic reflective particulate materials, e.g., comprising $TiO_2$, ZnO or $ZrO_2$ are commercially available from a number of sources. Nonlimiting examples of suitable particulate materials are available from Warner Jenkinson (C-9729, a hydrophobic, dimethicone treated, anatase form $TiO_2$); U.S. Cosmetics (TRONOX $TiO_2$ series, e.g., AT-T-CR837, a hydrophilic, rutile, amino acid treated $TiO_2$; AT-T-328, a hydrophilic, anatase, amino acid treated $TiO_2$; and SAT-T CR837, a rutile $TiO_2$); and Kobo (Kobo GLW75CAP, i.e., a predispersion of ammonium polyacrylate treated $TiO_2$, glycerin, and water or TRONOX $TiO_2$ series, e.g., ST490, a rutile, silane treated $TiO_2$). The particulate materials are available in essentially neat, powdered form or predispersed in various types of dispersants, including but not limited to isopropyl isostearate, isopropyl palmitate, methyl isostearate, Finsolv TN, cylcomethicone, and cyclomethicone and dimethicone copolyols.

The relective particulate material useful in the compositions of the present invention will generally have a refractive index of at least about 2, more preferably at least about 2.5 (e.g., from about 2 to about 3). Refractive index can be determined by conventional methods. For example, a method for determining the refractive index which is applicable to the present invention is described in J. A. Dean, Ed., Lange's Handbook of Chemistry, 14th Ed., McGraw Hill, New York, 1992, Section 9, Refractometry.

C. Structuring Agent

The present compositions can optionally contain a structuring agent. Structuring agents are particularly preferred in the oil-in-water emulsions of the present invention. Without being limited by theory, it is believed that the structuring agent assists in providing rheological characteristics to the composition which contribute to the stability of the composition. For example, the structuring agent tends to assist in the formation of the liquid crystalline gel network structures. The structuring agent may also function as an emulsifier or surfactant. Preferred compositions of this invention comprise from about 1% to about 20%, more preferably from about 1% to about 10%, most preferably from about 2% to about 9%, of one or more structuring agents.

Preferred structuring agents are those having an HLB of from about 1 to about 6 and having a melting point of at least about 45° C. Suitable structuring agents are those selected from the group consisting of saturated $C_{14}$ to $C_{30}$ fatty alcohols, saturated $C_{16}$ to $C_{30}$ fatty alcohols containing from about 1 to about 5 moles of ethylene oxide, saturated $C_{16}$ to $C_{30}$ diols, saturated $C_{16}$ to $C_{30}$ monoglycerol ethers, saturated $C_{16}$ to $C_{30}$ hydroxy fatty acids, $C_{14}$ to $C_{30}$ hydroxylated and nonhydroxylated saturated fatty acids, $C_{14}$ to $C_{30}$ saturated ethoxylated fatty acids, amines and alcohols containing from about 1 to about 5 moles of ethylene oxide diols, $C_{14}$ to $C_{30}$ saturated glyceryl mono esters with a monoglyceride content of at least 40%, $C_{14}$ to $C_{30}$ saturated polyglycerol esters having from about 1 to about 3 alkyl group and from about 2 to about 3 saturated glycerol units, $C_{14}$ to $C_{30}$ glyceryl mono ethers, $C_{14}$ to $C_{30}$ sorbitan mono/diesters, $C_{14}$ to $C_{30}$ saturated ethoxylated sorbitan mono/diesters with about 1 to about 5 moles of ethylene oxide, $C_{14}$ to $C_{30}$ saturated methyl glucoside esters, $C_{14}$ to $C_{30}$ saturated sucrose mono/diesters, $C_{14}$ to $C_{30}$ saturated ethoxylated methyl glucoside esters with about 1 to about 5 moles of ethylene oxide, $C_{14}$ to $C_{30}$ saturated polyglucosides having an average of between 1 to 2 glucose units and mixtures thereof, having a melting point of at least about 45° C.

The preferred structuring agents of the present invention are selected from the group consisting of stearic acid, palmitic acid, stearyl alcohol, cetyl alcohol, behenyl alcohol, stearic acid, palmitic acid, the polyethylene glycol ether of stearyl alcohol having an average of about 1 to about 5 ethylene oxide units, the polyethylene glycol ether of cetyl alcohol having an average of about 1 to about 5 ethylene oxide units, and mixtures thereof. More preferred structuring agents of the present invention are selected from the group consisting of stearyl alcohol, cetyl alcohol, behenyl alcohol, the polyethylene glycol ether of stearyl alcohol having an average of about 2 ethylene oxide units (steareth-2), the polyethylene glycol ether of cetyl alcohol having an average of about 2 ethylene oxide units, and mixtures thereof. Even more preferred structuring agents are selected from the group consisting of stearic acid, palmitic acid, stearyl alcohol, cetyl alcohol, behenyl alcohol, steareth-2, and mixtures thereof.

D. Skin Care Active

The compositions of the invention can optionally comprise a safe and effective amount of a skin care active, preferably from about 0.1% to about 20%, more preferably from about 0.15% to abut 10%, and most preferably from about 0.2% to about 7.5%. Such materials are those which manifest skin appearance benefits following chronic application of the composition containing such materials. Materials providing such benefits include, but are not limited to, Vitamin $B_3$ compounds, retinoids, anti-oxidants/radical scavengers, and combinations thereof.

Specific examples of these actives include the following.

1) Vitamin $B_3$ Compounds

Vitamin $B_3$ compounds enhance the skin conditioning benefits of the present invention, including regulating signs of skin aging, more especially wrinkles, lines, and pores. The compositions of the present invention preferably comprise from about 0.01% to about 50%, more preferably from about 0.1% to about 10%, even more preferably from about 0.5% to about 10%, and still more preferably from about 1% to about 5%, most preferably from about 2% to about 5%, of the vitamin $B_3$ compound.

As used herein, "vitamin $B_3$ compound" means a compound having the formula:

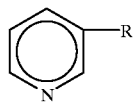

wherein R is —$CONH_2$ (i.e., niacinamide), —COOH (i.e., nicotinic acid) or —$CH_2OH$ (i.e., nicotinyl alcohol); derivatives thereof; and salts of any of the foregoing.

Exemplary derivatives of the foregoing vitamin $B_3$ compounds include nicotinic acid esters, including non-vasodilating esters of nicotinic acid, nicotinyl amino acids, nicotinyl alcohol esters of carboxylic acids, nicotinic acid N-oxide and niacinamide N-oxide.

Suitable esters of nicotinic acid include nicotinic acid esters of $C_1$–$C_{22}$, preferably $C_1$–$C_{16}$, more preferably $C_1$–$C_6$ alcohols. The alcohols are suitably straight-chain or branched chain, cyclic or acyclic, saturated or unsaturated (including aromatic), and substituted or unsubstituted. The esters are preferably non-vasodilating. As used herein, "non-vasodilating" means that the ester does not commonly yield a visible flushing response after application to the skin in the subject compositions (the majority of the general population would not experience a visible flushing response, although such compounds may cause vasodilation not visible to the naked eye, i.e., the ester is non-rubifacient). Non-vasodilating esters of nicotinic acid include tocopherol nicotinate and inositol hexanicotinate; tocopherol nicotinate is preferred.

Other derivatives of the vitamin $B_3$ compound are derivatives of niacinamide resulting from substitution of one or more of the amide group hydrogens. Nonlimiting examples of derivatives of niacinamide useful herein include nicotinyl amino acids, derived, for example, from the reaction of an activated nicotinic acid compound (e.g., nicotinic acid azide or nicotinyl chloride) with an amino acid, and nicotinyl alcohol esters of organic carboxylic acids (e.g., C1–C18). Specific examples of such derivatives include nicotinuric acid ($C_8H_8N_2O_3$) and nicotinyl hydroxamic acid ($C_6H_6N_2O_2$), which have the following chemical structures:

nicotinuric acid:

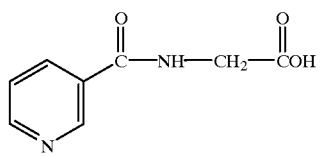

nicotinyl hydroxamic acid:

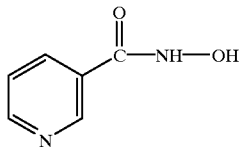

Exemplary nicotinyl alcohol esters include nicotinyl alcohol esters of the carboxylic acids salicylic acid, acetic acid, glycolic acid, palmitic acid and the like. Other non-limiting examples of vitamin $B_3$ compounds useful herein are 2-chloronicotinamide, 6-aminonicotinamide, 6-methylnicotinamide, n-methyl-nicotinamide, n,n-diethylnicotinamide, n-(hydroxymethyl)-nicotinamide, quinolinic acid imide, nicotinanilide, n-benzylnicotinamide, n-ethylnicotinamide, nifenazone, nicotinaldehyde, isonicotinic acid, methyl isonicotinic acid, thionicotinamide, nialamide, 1-(3-pyridylmethyl) urea, 2-mercaptonicotinic acid, nicomol, and niaprazine.

Examples of the above vitamin $B_3$ compounds are well known in the art and are commercially available from a number of sources, e.g., the Sigma Chemical Company (St. Louis, Mo.); ICN Biomedicals, Inc. (Irvin, Calif.) and Aldrich Chemical Company (Milwaukee, Wis.).

One or more vitamin $B_3$ compounds may be used herein. Preferred vitamin $B_3$ compounds are niacinamide and tocopherol nicotinate. Niacinamide is more preferred.

When used, salts, derivatives, and salt derivatives of niacinamide are preferably those having substantially the same efficacy as niacinamide in the methods of regulating skin condition described herein.

Salts of the vitamin $B_3$ compound are also useful herein. Nonlimiting examples of salts of the vitamin $B_3$ compound useful herein include organic or inorganic salts, such as inorganic salts with anionic inorganic species (e.g., chloride, bromide, iodide, carbonate, preferably chloride), and organic carboxylic acid salts (including mono-, di- and tri-C1–C18 carboxylic acid salts, e.g., acetate, salicylate, glycolate, lactate, malate, citrate, preferably monocarboxylic acid salts such as acetate). These and other salts of the vitamin $B_3$ compound can be readily prepared by the skilled artisan, for example, as described by W. Wenner, "The Reaction of L-Ascorbic and D-Iosascorbic Acid with Nicotinic Acid and Its Amide", J. Organic Chemistry, VOL. 14, 22–26 (1949), which is incorporated herein by reference. Wenner describes the synthesis of the ascorbic acid salt of niacinamide.

In a preferred embodiment, the ring nitrogen of the vitamin $B_3$ compound is substantially chemically free (e.g., unbound and/or unhindered), or after delivery to the skin becomes substantially chemically free ("chemically free" is hereinafter alternatively referred to as "uncomplexed"). More preferably, the vitamin $B_3$ compound is essentially uncomplexed. Therefore, if the composition contains the vitamin $B_3$ compound in a salt or otherwise complexed form, such complex is preferably substantially reversible, more preferably essentially reversible, upon delivery of the composition to the skin. For example, such complex should be substantially reversible at a pH of from about 5.0 to about 6.0. Such reversibility can be readily determined by one having ordinary skill in the art.

More preferably the vitamin $B_3$ compound is substantially uncomplexed in the composition prior to delivery to the skin. Exemplary approaches to minimizing or preventing the formation of undesirable complexes include omission of materials which form substantially irreversible or other complexes with the vitamin $B_3$ compound, pH adjustment, ionic strength adjustment, the use of emulsifiers, and formulating wherein the vitamin $B_3$ compound and materials which complex therewith are in different phases. Such approaches are well within the level of ordinary skill in the art.

Thus, in a preferred embodiment, the vitamin $B_3$ compound contains a limited amount of the salt form and is more preferably substantially free of salts of a vitamin $B_3$ compound. Preferably the vitamin $B_3$ compound contains less than about 50% of such salt, and is more preferably essentially free of the salt form. The vitamin $B_3$ compound in the compositions hereof having a pH of from about 4 to about 7 typically contain less than about 50% of the salt form.

The vitamin $B_3$ compound may be included as the substantially pure material, or as an extract obtained by suitable physical and/or chemical isolation from natural (e.g., plant) sources. The vitamin $B_3$ compound is preferably substantially pure, more preferably essentially pure.

2) Retinoids

Retinoids enhance the skin appearance benefits of the present invention, especially in regulating skin condition, including regulating signs of skin aging, more especially wrinkles, lines, and pores.

As used herein, "retinoid" includes all natural and/or synthetic analogs of Vitamin A or retinol-like compounds which possess the biological activity of Vitamin A in the skin as well as the geometric isomers and stereoisomers of these compounds. The retinoid is preferably retinol, retinol esters (e.g., $C_2$–$C_{22}$ alkyl esters of retinol, including retinyl palmitate, retinyl acetate, retinyl propionate), retinal, and/or retinoic acid (including all-trans retinoic acid and/or 13-cis-retinoic acid), more preferably retinoids other than retinoic acid. These compounds are well known in the art and are commercially available from a number of sources, e.g., Sigma Chemical Company (St. Louis, Mo.), and Boerhinger Mannheim (Indianapolis, Ind.). Other retinoids which are useful herein are described in U.S. Pat. Nos. 4,677,120, issued Jun. 30, 1987 to Parish et al.; 4,885,311, issued Dec. 5, 1989 to Parish et al.; 5,049,584, issued Sep. 17, 1991 to Purcell et al.; 5,124,356, issued Jun. 23, 1992 to Purcell et al.; and Reissue 34,075, issued Sep. 22, 1992 to Purcell et al. Other suitable retinoids are tocopheryl-retinoate [tocopherol ester of retinoic acid (trans- or cis-), adapalene {6-[3-(1-adamantyl)-4-methoxyphenyl]-2-naphthoic acid}, and tazarotene (ethyl 6-[2-(4,4-dimethylthiochroman-6-yl)-ethynyl]nicotinate). One or more retinoids may be used herein. Preferred retinoids are retinol, retinyl palmitate, retinyl acetate, retinyl proprionate, retinal and combinations thereof. More preferred are retinol and retinyl proprionate.

The retinoid may be included as the substantially pure material, or as an extract obtained by suitable physical and/or chemical isolation from natural (e.g., plant) sources. The retinoid is preferably substantially pure, more preferably essentially pure.

The compositions of this invention contain a safe and effective amount of the retinoid, such that the resultant composition is safe and effective for regulating skin condition, preferably for regulating visible and/or tactile discontinuities in skin, more preferably for regulating signs of skin aging, even more preferably for regulating visible and/or tactile discontinuities in skin texture associated with skin aging. The compositions preferably contain from or about 0.005% to or about 2%, more preferably 0.01% to or about 2%, retinoid. Retinol is most preferably used in an amount of from or about 0.01% to or about 0.15%; retinol esters are most preferably used in an amount of from or about 0.01% to or about 2% (e.g., about 1%); retinoic acids are most preferably used in an amount of from or about 0.01% to or about 0.25%; tocopheryl-retinoate, adapalene, and tazarotene are most preferably used in an amount of from or about 0.01% to or about 2%.

In a preferred embodiment, the composition contains both a retinoid and a Vitamin $B_3$ compound. The retinoid is preferably used in the above amounts, and the vitamin $B_3$ compound is preferably used in an amount of from or about 0.1% to or about 10%, more preferably from or about 2% to or about 5%.

3) Anti-Oxidants/Radical Scavengers

Compositions of the present invention can optionally include an anti-oxidant/radical scavenger. The anti-oxidant/radical scavenger is especially useful for providing protection against UV radiation which can cause increased scaling or texture changes in the stratum corneum and against other environmental agents which can cause skin damage.

A safe and effective amount of an anti-oxidant/radical scavenger may be added to the compositions of the subject invention, preferably from about 0.1% to about 10%, more preferably from about 1% to about 5%, of the composition.

Anti-oxidants/radical scavengers such as ascorbic acid (vitamin C) and its salts, ascorbyl esters of fatty acids, ascorbic acid derivatives (e.g., magnesium ascorbyl phosphate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, lysine, methionine, proline, superoxide dismutase, silymarin, tea extracts, grape skin/seed extracts, melanin, and rosemary extracts may be used. Preferred anti-oxidants/radical scavengers are selected from tocopherol sorbate and other esters of tocopherol, more preferably tocopherol sorbate. For example, the use of tocopherol sorbate in topical compositions and applicable to the present invention is described in U.S. Pat. No. 4,847,071, issued on Jul. 11, 1989 to Donald L. Bissett, Rodney D. Bush and Ranjit ChatteJee.

4) Organic Hydroxy Acids

Compositions of the present invention can optionally comprise an organic hydroxy acid. Suitable hydroxy acids include $C_1$–$C_{18}$ hydroxy acids, preferably $C_8$ or below. The hydroxy acids can be substituted or unsubstituted, straight chain, branched chain or cyclic (preferably straight chain), and saturated or unsaturated (mono- or poly- unsaturated) (preferably saturated). Non-limiting examples of suitable hydroxy acids include salicylic acid, glycolic acid, lactic acid, 5 octanoyl salicylic acid, hydroxyoctanoic acid, hydroxycaprylic acid, and lanolin fatty acids. Preferred concentrations of the organic hydroxy acid range from about 0.1% to about 10%, more preferably from about 0.2% to about 5%, also preferably from about 0.5% to about 2%. Salicylic acid is preferred. The organic hydroxy acids enhance the skin appearance benefits of the present invention. For example, the organic hydroxy acids tend to improve the texture of the skin.

E. Additional Skin Conditioning Components

Preferred compositions of the present invention optionally comprise additional skin conditioning components. These skin conditioning components are useful for lubricating the skin, increasing the smoothness and suppleness of the skin, preventing or relieving dryness of the skin, hydrating the skin, and/or protecting the skin. These skin conditioning components enhance the skin appearance improvements of the present invention. The additional skin conditioning component is preferably selected from the group consisting of additional emollients (e.g., medium and heavy), humectants, mosturizers, and mixtures thereof. (These additional skin conditioning components may be categorized or described herein by their cosmetic and/or therapeutic benefit or their postulated mode of action. However, it is to be understood that the skin conditioning components useful herein can in some instances provide more than one cosmetic and/or therapeutic benefit such as absorbency, structuring, etc. or operate via more than one mode of action. Therefore, classifications herein are made for the sake of convenience and are not intended to limit an ingredient to the particularly stated application or applications listed).

The skin conditioning component is preferably present at a level of at least about 0.1%, more preferably from about 1% to about 99%, even more preferably from about 1% to about 50%, still more preferably from about 2% to about 30% and most preferably from about 5% to about 25% (e.g., about 5% to about 10% or 15%).

Suitable emollients may be selected from one or more of the following classes: triglyceride esters which include, but are not limited to, vegetable and animal fats and oils such as castor oil cocoa butter, safflower oil, cottonseed oil, corn oil, olive oil, cod liver oil, almond oil, avocado oil, palm oil, sesame oil, squalene, kikui oil and soybean oil; acetoglyceride esters, such as acetylated monoglycerides; ethoxylated glycerides, such as ethoxylated glyceryl monostearate; alkyl esters of fatty acids having 10 to 20 carbon atoms which include, but are not limited to, methyl, isopropyl, and butyl esters of fatty acids such as hexyl laurate, isohexyl laurate, isohexyl palmitate, methyl palmitate, decyloleate, isodecyl oleate, hexadecyl stearate decyl stearate, diisopropyl adipate, diisohexyl adipate, dihexyldecyl adipate, diisopropyl sebacate, lauryl lactate, myristyl lactate, and cetyl lactate; alkenyl esters of fatty acids having 10 to 20 carbon atoms such as oleyl myristate, oleyl stearate, and oleyl oleate; fatty acids having 10 to 20 carbon atoms such as pelargonic, lauric, myristic, palmitic, stearic, isostearic, hydroxystearic, oleic, linoleic, ricinoleic, arachidic, behenic, and erucic acids; fatty alcohols having 10 to 20 carbon atoms such as lauryl, myristyl, cetyl, hexadecyl, stearyl, isostearyl, hydroxystearyl, oleyl, ricinoleyl, behenyl, erucyl, and 2-octyl dodecanyl alcohols; lanolin and lanolin derivatives such as lanolin, lanolin oil, lanolin wax, lanolin alcohols, lanolin fatty acids, isopropyl lanolate, ethoxylated cholesterol, propoxylated lanolin alcohols, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, and liquid and semisolid lanolin absorption bases; Polyhydric alcohol esters such as ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol polyfatty esters, ethoxylated glyceryl monostearate, 1,2-butylene glycol monostearate, 1,2-butylene glycol distearate, sorbitan fatty acid esters, and polyoxyethylene sorbitan fatty acid esters; wax esters such as beeswax, spermaceti, myristyl myristate, stearyl stearate; beeswax derivatives such as polyoxyethylene sorbitol beeswax which are reaction products of beeswax with ethoxylated sorbitol of varying ethylene oxide content, forming a mixture of ether esters; vegetable waxes including, but not limited to, carnauba and candelilla waxes; phospholipids such as lecithin and derivatives; sterols including, but not limited to, cholesterol and cholesterol fatty acid esters; and amides such as fatty acid amides, ethoxylated fatty acid amides, and solid fatty acid alkanolamides.

Suitable humectants include those of the polyhydric alcohol-type. Typical polyhydric alcohols include polyalkylene glycols and more preferably alkylene polyols and their derivatives, including propylene glycol, dipropylene glycol, polypropylene glycol, polyethylene glycol and derivatives thereof (e.g., PEG-2, PEG-3, PEG-30, PEG-500, etc.), sorbitol, hydroxypropyl sorbitol, erythritol, threitol, pentaerythritol, xylitol, glucitol, mannitol, hexylene glycol, butylene glycol (e.g., 1,3-butylene glycol), hexane triol (e.g., 1,2,6-hexanetriol), glycerol, ethoxylated glycerol, propoxylated glycerol, sodium 2-pyrrolidone-5-carboxylate, soluble collagen, dibutyl phthalate, gelatin and mixtures thereof.

Also useful herein are guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); sugar and starch derivatives (e.g., alkoxylated glucose); hyaluronic acid and derivatives thereof (e.g., salt derivatives such as sodium hyaluraonate); lactamide monoethanolamine; acetamide monoethanolamine; urea; panthenol; sugars; starches; silicone fluids; silicone gums; and mixtures thereof. Also useful are the propoxylated glycerols described in U.S. Pat. No. 4,976,953. Other useful conditioning compounds include the various $C_1$–$C_{30}$ monoesters and polyesters of sugars and related materials such as described herein in reference to the hydrophobic phase of the emulsion.

F. Sunscreens and Sunblocks

Exposure to ultraviolet light can result in excessive scaling and texture changes of the stratum corneum. Therefore, the compositions of the subject invention preferably contain a sunscreen or sunblock. Suitable sunscreens or sunblocks may be organic or inorganic.

A wide variety of conventional sunscreening agents are suitable for use herein. Sagarin, et al., at Chapter VIII, pages 189 et seq., of *Cosmetics Science and Technology* (1972), discloses numerous suitable agents, and is incorporated herein by reference. Specific suitable sunscreening agents include, for example: p-aminobenzoic acid, its salts and its derivatives (ethyl, isobutyl, glyceryl esters; p-dimethylaminobenzoic acid); anthranilates (i.e., o-aminobenzoates; methyl, menthyl, phenyl, benzyl, phenylethyl, linalyl, terpinyl, and cyclohexenyl esters); salicylates (amyl, phenyl, octyl, benzyl, menthyl, glyceryl, and di-propyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylacetoumbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy- substituted benzophenones; uric and violuric acids; tannic acid and its derivatives (e.g., hexaethylether); (butyl carbotol) (6-propyl piperonyl) ether, hydroquinone; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; octocrylene; [3-(4'-methylbenzylidene bornan-2-one) and 4-isopropyl-di-benzoylmethane.

Of these, 2-ethylhexyl-p-methoxycinnamate (commercially available as PARSOL MCX), 4,4'-t-butyl methoxydibenzoyl-methane (commercially available as PARSOL 1789), 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl))aminobenzoate, 2-ethylhexyl-2cyano-3,3-diphenylacrylate, 2-ethylhexyl-salicylate, glyceryl-p-aminobenzoate, 3,3,5-tri-methylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene and mixtures of these compounds, are preferred.

More preferred organic sunscreens useful in the compositions useful in the subject invention are 2-ethylhexyl-p-methoxycinnamate, butylmethoxydibenzoyl-methane, 2-hydroxy-4-methoxybenzo-phenone, 2-phenylbenzimidazole-5-sulfonic acid, octyldimethyl-p-aminobenzoic acid, octocrylene and mixtures thereof.

Also particularly useful in the compositions are sunscreens such as those disclosed in U.S. Pat. No. 4,937,370 issued to Sabatelli on Jun. 26, 1990, and U.S. Pat. No. 4,999,186 issued to Sabatelli & Spirnak on Mar. 12, 1991. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

Preferred members of this class of sunscreening agents are 4-N,N-(2-ethylhexyl)methyl-aminobenzoic acid ester of 2,4-dihydroxybenzophenone; N,N-di-(2-etlylhexyl)-4-aminobenzoic acid ester with 4-hydroxydibenzoylmethane; 4-N,N-(2-ethylhexyl)methyl-aminobenzoic acid ester with 4-hydroxydibenzoylmethane; 4-N,N-(2-ethylhexyl)methyl-aminobenzoic acid ester of 2-hydroxy-4-(2-hydroxyethoxy) benzophenone; 4-N,N-(2-ethylhexyl)-methylaminobenzoic acid ester of 4-(2-hydroxyethoxy)dibenzoylmethane; N,N-di-(2-ethylhexyl)-4-aminobenzoic acid ester of 2-hydroxy-4-(2-hydroxyethoxy)benzophenone; and N,N-di-(2-ethylhexyl)-4-aminobenzoic acid ester of 4-(2-hydroxyethoxy)dibenzoylmethane and mixtures thereof.

Especially preferred sunscreens or sunblocks include butylmethoxydibenzoylmethane, 2-ethylhexyl-p-methoxycinnamate, phenyl benzimidazole sulfonic acid, and octocrylene.

A safe and effective amount of the sunscreen or sunblock is used, typically from about 1% to about 20%, more typically from about 2% to about 10%. Exact amounts will vary depending upon the sunscreen chosen and the desired Sun Protection Factor (SPF).

An agent may also be added to any of the compositions useful in the subject invention to improve the skin substantivity of those compositions, particularly to enhance their resistance to being washed off by water, or rubbed off. A preferred agent which will provide this benefit is a copolymer of ethylene and acrylic acid. Compositions comprising this copolymer are disclosed in U.S. Pat. 4,663,157, Brock, issued May 5, 1987.

G. Chelators

As used herein, "chelating agent" means an active agent capable of removing a metal ion from a system by forming a complex so that the metal ion cannot readily participate in or catalyze chemical reactions. The inclusion of a chelating agent is especially useful for providing protection against UV radiation which can contribute to excessive scaling or skin texture changes and against other environmental agents which can cause skin damage.

A safe and effective amount of a chelating agent may be added to the compositions of the subject invention, preferably from about 0.1% to about 10%, more preferably from about 1% to about 5%, of the composition. Exemplary chelators that are useful herein are disclosed in U.S. Pat. No. 5,487,884, issued Jan. 30, 1996 to Bissett et al.; International Publication No. 91/16035, Bush et al., published Oct. 31, 1995; and International Publication No. 91/16034, Bush et al., published Oct. 31, 1995. Preferred chelators useful in compositions of the subject invention are furildioxime and derivatives thereof.

The above listed compounds may be incorporated singly or in combination.

Methods for Regulating Skin Condition

The compositions of the present invention are useful for regulating skin condition (especially human skin, more especially human facial skin), including lubricating the skin, increasing the smoothness and suppleness of the skin, preventing or relieving dryness of the skin, hydrating the skin, and/or protecting the skin regulating visible and/or tactile discontinuities in skin, e.g., visible and/or tactile discontinuities in skin texture, more especially discontinuities associated with skin aging.

Regulating skin condition involves topically applying to the skin a safe and effective amount of a composition of the present invention. The amount of the composition which is applied, the frequency of application and the period of use will vary widely depending upon the active levels of a given composition and the level of regulation desired.

A wide range of quantities of the compositions of the present invention can be employed to provide a skin appearance and/or feel benefit. Quantities of the present compositions which are typically applied per application are, in mg composition/cm$^2$ skin, from about 0.1 mg/cm$^2$ to about 10 mg/cm$^2$. A particularly useful application amount is about 2.5 mg/cm$^2$. Typically applications would be on the order of about once per day, however application rates can vary from about once per week up to about three times per day or more.

Preferred compositions of this invention containing a reflective particulate material provide a visible improvement in skin condition essentially immediately following application of the composition to the skin. Such immediate improvement involves coverage or masking of skin imperfections such as textural discontinuities (including those associated with skin aging, such as enlarged pores), and/or providing a more even skin tone or color.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are given in CTFA name.

While particular embodiments of the subject invention have been described, it will be obvious to those skilled in the art that various changes and modifications to the subject invention can be made without departing from the spirit and scope of the invention. It is intended to cover, in the appended claims, all such modifications that are within the scope of the subject invention.

Examples 1–2

Oil-in-water emulsion compositions are prepared from the following ingredients using conventional formulating techniques.

|  | Example 1 | Example 2 |
| --- | --- | --- |
| Premix A |  |  |
| Water | QS100 | QS100 |
| Disodium EDTA | 0.10 | 0.10 |
| Carbopol 1382 | 0.10 | 0.10 |
| Carbopol 954 | 0.50 | 0.50 |
| Sorbitan Monostearate/Sucrose Cocoate | 1.00 | 1.00 |
| Glycerin | 7.00 | — |
| Premix B |  |  |
| Isopropyl Isostearate | 1.33 | 1.33 |
| Fatty acid ester of sugar[1] | 0.67 | 0.67 |
| Isohexadecane | — | 4.00 |

-continued

|  | Example 1 | Example 2 |
|---|---|---|
| Vitamin E Acetate | 0.50 | 0.50 |
| Silicone Treated TiO$_2$ (anatase) | 0.75 | — |
| Cetyl Alcohol | 0.72 | 0.72 |
| Stearyl Alcohol | 0.48 | 0.48 |
| PEG-100 Stearate | 0.10 | 0.10 |
| Stearic Acid | 0.10 | 0.10 |
| Vitamin E Acetate | 0.50 | 0.50 |
| Premix C | | |
| NaOH | 0.25 | 0.25 |
| Premix D | | |
| Water | — | 5.00 |
| Kobo GLW75CAP[2] | — | 0.534 |
| Glycerin | — | 6.93 |
| Premix E | | |
| Water | 5.00 | 5.00 |
| Dexpanthenol | 0.50 | 0.50 |
| Niacinamide | 2.00 | 2.00 |
| Preservative | 0.10 | 0.10 |
| Premix F | | |
| Dimethicone (and) Dimethiconol | 2.00 | 2.00 |

[1] A C1–C30 monoester or polyester of sugars and one or more carboxylic acid moieties as described herein, preferably a sucrose polyester in which the degree of esterification is 7–8, and in which the fatty acid moieties are C18 mono- and/or di-unsaturated and behenic, in a molar ratio of unsaturates:behenic of 1:7 to 3:5, more preferably the octaester of sucrose in which there are about 7 behenic fatty acid moieties and about 1 oleic acid moiety in the molecule, e.g., sucrose ester of cottonseed oil fatty acids, e.g., SEFA Cottonate.
[2] A predispersion of ammonium polyacrylate treated TiO$_2$, water, and glycerin.

First, mix (using propeller type mixer) Premix A ingredients in a suitable size vessel and heat to 70–75° C. In a separate vessel mix Premix B ingredients and heat to 70–75° C. At 70–75° C., add Premix B to Premix A while continuing to mix. Then add Premix C to the batch mixture of Premixes A/B while continuing to mix. The Premix C component allows neutralization of the mixture. In a separate vessel, mix Premix D until uniform and then add to the batch mixture of Premixes A/B/C while continuing to mix. Cool to 50° C. Combine Premix E ingredients until uniform and then add to the batch of Premixes A-D while continuing to mix. Then add Premix F ingredient to the batch mixture of A–E and continue to cool to about 35° C. Mixing is continued until the resulting batch mixture is uniform. Once batch mixture is uniform, resulting composition is introduced into a suitable dispenser as described herein.

Examples 3–6

Oil-in-water emulsion compositions are prepared from the following ingredients using conventional formulating techniques.

|  | Example 3 | Example 4 | Example 5 | Example 6 |
|---|---|---|---|---|
| Premix A | | | | |
| Water | QS100 | QS100 | QS100 | QS100 |
| Disodium EDTA | 0.10 | 0.10 | 0.10 | 0.10 |
| Sorbitan Monostearate/Sucrose Cocoate | 1.00 | 1.00 | 1.00 | 1.00 |
| Premix B | | | | |
| Isopropyl Isostearate | 1.33 | 1.33 | 1.33 | 1.33 |
| Fatty acid ester of sugar[1] | 0.67 | 0.67 | 0.67 | 0.67 |
| Isohexadecane | 3.00 | 3.00 | 3.00 | 3.00 |
| Vitamin E Acetate | 0.50 | 0.50 | 0.50 | 0.50 |
| Cetyl Alcohol | 0.72 | 0.72 | 0.72 | 0.72 |
| Stearyl Alcohol | 0.48 | 0.48 | 0.48 | 0.48 |
| PEG-100 Stearate | 0.10 | 0.10 | 0.10 | 0.10 |
| Stearic Acid | 0.10 | 0.10 | 0.10 | 0.10 |
| Premix C | | | | |
| NaOH | 0.013 | 0.013 | 0.010 | 0.013 |
| Premix D | | | | |
| Water | 5.00 | 5.00 | 5.00 | — |
| Kobo GLW75CAP[2] | 0.543 | 0.543 | 0.543 | — |
| Glycerin | 6.93 | 6.93 | 6.93 | — |
| Premix E | | | | |
| Sepigel 305[3] | 2.50 | 2.50 | 1.50 | 2.50 |
| Premix F | | | | |
| Water | 5.00 | 5.00 | 5.00 | 5.00 |
| Dexpanthenol | 0.50 | 0.50 | 0.25 | — |
| Niacinamide | 2.00 | 5.00 | 5.00 | — |
| Preservative | 0.10 | 0.10 | 0.10 | 0.10 |
| Premix G | | | | |
| Dimethicone (and) Dimethiconol | 2.00 | 2.00 | 2.00 | 2.00 |

[1] A C1–C30 monoester or polyester of sugars and one or more carboxylic acid moieties as described herein, preferably a sucrose polyester in which the degree of esterification is 7–8, and in which the fatty acid moieties are C18 mono- and/or di-unsaturated and behenic, in a molar ratio of unsaturates:behenic of 1:7 to 3:5, more preferably the octaester of sucrose in which there are about 7 behenic fatty acid moieties and about 1 oleic acid moiety in the molecule, e.g., sucrose ester of cottonseed oil fatty acids, e.g., SEFA Cottonate.
[2] A predispersion of ammonium polyacrylate treated TiO$_2$, water, and glycerin.
[3] A mixture of polyacrylamide, isoparaffin, laureth-7.

Mix Premixes A–D as described above in Examples 1–2 and cool mixture to 60° C. Combine Premix E ingredients until uniform and then add to the batch of Premixes A–D while continuing to mix. Cool mixture to 50° C. Then add Premixes F and G to the batch mixture of A–E and continue to cool to about 35° C. Mixing is continued until the resulting batch mixture is uniform. Once batch mixture is uniform, resulting composition is introduced into a suitable dispenser as described herein.

Examples 7–8

Oil-in-water emulsion compositions are prepared from the following ingredients using conventional formulating techniques.

|  | Example 7 | Example 8 |
|---|---|---|
| Premix A | | |
| Water | QS100 | QS100 |
| Disodium EDTA | 0.10 | 0.10 |
| Sorbitan Monostearate/Sucrose Cocoate | — | 1.00 |
| Acrylates/C10–C30 Alkyl Acrylate | 0.10 | 0.05 |
| Premix B | | |
| Isopropyl Isostearate | 1.10 | 1.4 |
| Caprylic/Capric Acid | 1.15 | 1.35 |
| Isohexadecane | 2.00 | 2.00 |
| Vitamin E Acetate | 0.25 | 0.25 |
| Cetyl Alcohol | 0.72 | 0.72 |
| Cetyl Ricinoleate | 1.00 | 0.50 |
| Stearyl Alcohol | 0.48 | 0.48 |
| PEG-100 Stearate | — | 0.10 |

-continued

|  | Example 7 | Example 8 |
|---|---|---|
| Steareth-21 | 0.56 | — |
| Steareth-2 | 0.06 | — |
| Stearic Acid | — | 0.10 |
| Premix C | | |
| NaOH | 0.043 | 0.025 |
| Premix D | | |
| Water | 5.00 | 5.00 |
| Kobo GLW75CAP[1] | 0.543 | 0.543 |
| Glycerin | 6.93 | 6.93 |
| Premix E | | |
| Sepigel 305[2] | 1.85 | 1.40 |
| Premix F | | |
| Water | 5.00 | 5.00 |
| Dexpanthenol | 0.50 | 0.25 |
| Niacinamide | 2.00 | 2.00 |
| Preservative | 0.10 | 0.10 |
| Premix G | | |
| Dimethicone (and) Dimethiconol | 3.00 | 3.00 |

[1] A predispersion of ammonium polyacrylate treated TiO$_2$, water, and glycerin.
[2] A mixture of polyacrylamide, isoparaffin, laureth-7

Prepare Examples 7–8 as described in Examples 3–6.

What is claimed:

1. A skin care kit comprising a skin care composition contained within a dispenser wherein the skin care composition comprises:
   a) an emulsion which comprises:
      1) at least one hydrophobic phase comprising an oil and from about 0.1% to about 20%, by weight of the composition, of a light emollient;
      2) at least one hydrophilic phase comprising water; and
      3) from about 0.1% to about 5%, by weight of the composition, of an emulsifier having an HLB of at least 6;
   wherein the composition has a viscosity of from about 15,000 cps to about 200,000 cps and a pH of from about 3 to about 9; and
   b) the dispenser for the skin care composition comprises a container for storing a supply of the skin care composition to be dispensed, said container having a bottom portion and an upper portion, said bottom portion having a slidable follower piston and said upper portion having a pump for dispensing the skin care composition, said pump comprising:
      1) a first non-return valve (16) provided in an upper partition wall of the container for controlling communication between the interior of the container and a pump chamber through a first opening (12) formed in said partition wall (11);
      2) a guide sleeve arrangement (6) surrounding said first opening (12) and having first non-return valve (16) pivotally connected thereto, said guide sleeve arrangement extending upwardly from said partition wall to define circumferentially said pump chamber (24), said guide sleeve arrangement (6) having inner and outer circumferential guide sleeves, said first non-return valve being pivotally connected to said inner guide sleeve;
      3) a cup-shaped actuator cap (7) having a peripheral downwardly projecting outer wall portion and an inner tubular section (19), the latter forming a discharge channel having a laterally outwardly opening outlet passage, wherein:
         (a) said outer wall portion of the actuator cap (7) is slidably engaged with the outer circumferential guide sleeve of the guide sleeve arrangement (6), both being provided with co-operating stop projections (26, 27) to limit axial upward movement of the actuator cap (7),
         (b) said outer guide sleeve being integral with said upper partition wall of said container, and providing an upper radially outwardly projecting rim portion (25) spaced from the stop projection (26) of the guide sleeve arrangement (6) to establish a circumferential guide surface engaging an inner guide surface of the outer wall portion of the actuator cap,
         (c) said tubular section of the actuator cap having a downwardly extending portion having a diameter greater than that of said laterally opening outlet passage and supporting a dispensing piston (22) to keep the piston (22) slidably engaged with said inner circumferential guide sleeve of said guide sleeve arrangement (6), thereby defining a space forming the pump chamber (24),
         (d) said dispensing piston (22) having a second opening (29) in register with the tubular section of the actuator cap (7),
         (e) said second opening (29) being controlled by a second non-return valve (3) for controlling communication between the pump chamber upstream thereof and the discharge channel of the actuator cap downstream thereof; and
      4) a return spring (32) extending between a stationary portion of the inner guide sleeve and the actuator cap (7) to bias said actuator cap (7) into a rest position;
   wherein said pump is suitable for dispensing per activation an amount of said skin care composition sufficient to provide from about 0.1 mg/cm$^2$ of skin surface to about 10 mg/cm$^2$ of skin surface per application.

2. The skin care kit of claim 1 wherein the emulsion is an oil-in-water emulsion.

3. The skin care kit of claim 1 wherein the composition comprises from about 0.15% to about 10%, by weight of the composition, of the light emollient.

4. The skin care kit of claim 3 wherein the composition comprises from about 0.20% to about 5%, by weight of the composition, of the light emollient.

5. The skin care kit of claim 1 wherein the light emollient is selected from the group consisting of isohexadecane, isododecane, isoeicosane, $C_{9-16}$ isoparaffin, light mineral oil, isopropyl isostearate, methyl isostearate, ethyl isostearate, isononyl isonononoate, octyl palmitate, isopropyl myristate, isopropyl palmitate, diisopropyl sebacate, hexyl laurate, $C_{12-15}$ alcohol benzoate, dioctyl maleate, diisopropyl adipate, $C_{12-15}$ alcohol salicylate, hydrogenated polyisobutene, octyl salicylate, cylomethicone, dimethicone, dimethiconol, and mixtures thereof.

6. The skin care kit of claim 5 wherein the light emollient is selected from the group consisting of isohexadecane, isopropyl isostearate, methyl isostearate, ethyl isostearate, isononyl isonononoate, isopropyl myristate, isopropyl palmitate, dimethicone, and mixtures thereof.

7. The skin care kit of claim 6 wherein the light emollient is selected from the group consisting of isohexadecane, isopropyl isostearate, methyl isostearate, ethyl isostearate, isononyl isonononoate, dimethicone, and mixtures thereof.

8. The skin care kit of claim 1 wherein the emulsifier is selected from the group consisting of sorbitan monostearate, sucrose cocoate, steareth-10, steareth-20, steareth-21, steareth-100, oleth-10, oleth-20, laureth-23, cetearyl glucoside, ceteth-10, ceteth-20, PEG-100 stearate, and mixtures thereof.

9. The skin care kit of claim 1 wherein the composition has a viscosity of from about 20,000 cps to about 100,000 cps.

10. The skin care kit of claim 9 wherein the composition has a viscosity of from about 25,000 cps to about 60,000 cps.

11. The skin care kit of claim 10 wherein the composition further comprises a thickening agent.

12. The skin care kit of claim 11 wherein the thickening agent is a polymeric thickening agent and the composition comprises from about 0.1% to about 5%, by weight of the composition, of the polymeric thickening agent.

13. The skin care kit of claim 12 wherein the composition comprises from about 0.2% to about 3%, by weight of the composition, of the polymeric thickening agent.

14. The skin care kit of claim 12 wherein the polymeric thickening agent is selected from the group consisting of carboxylic acid polymers, crosslinked polyacrylate polymers, polyacrylamide polymers, acrylates/$C_{10}$–$C_{30}$ alkyl acrylate crosspolymers, crosslinked alkyl vinyl ethers and maleic anhydride copolymers, crosslinked poly(N-vinylpyrrolidones), polysaccharides, and mixtures thereof.

15. The skin care kit of claim 1 wherein the hydrophobic phase further comprises from about 0.1% to about 10%, by weight of the composition, of an organopolysiloxane oil.

16. The skin care kit of claim 15 wherein the organopolysiloxane oil selected from the group consisting of cyclomethicone, dimethicone, dimethiconol, and mixtures thereof.

17. The skin care kit of claim 1 wherein the composition further comprises from about 0.1% to about 2%, by weight of the composition, of a reflective particulate material.

18. The skin care kit of claim 17 wherein the reflective particulate material is charged and has an average, primary, neat particle size of from about 100 nm to about 300 nm.

19. The skin care kit of claim 18 wherein the charged reflective particulate material comprises a metallic oxide, said metallic oxide being coated with a coating material which confers a net charge that is greater than the zeta potential of said uncoated metallic oxide.

20. The skin care kit of claim 18 wherein the reflective particulate material is selected from the group consisting of $TiO_2$, $ZnO$, $ZrO_2$, and mixtures thereof.

21. The skin care kit of claim 20 wherein the metallic oxide consists essentially of $TiO_2$.

22. The skin care kit of claim 1 wherein the composition further comprises from about 0.1% to about 20%, by weight of the composition, of a skin care active.

23. The skin care kit of claim 22 wherein the skin care active is selected from the group consisting of vitamin $B_3$ compounds, retinoids, anti-oxidants, radical scavengers, and mixtures thereof.

24. The skin care kit of claim 23 wherein the skin care active is niacinamide.

25. The skin care kit of claim 1 wherein the composition further comprises an additional skin conditioning component selected from the group consisting of medium emollients, heavy emollients, humectants, and moisturizers, and mixtures thereof.

26. The skin care kit of claim 1 wherein the dispenser is characterized in that said guide sleeve arrangement consists of an integrally formed guide sleeve (38) having a U-shaped wall (39, 40) in cross-section.

27. A skin care kit according to claim 26 wherein the skin care composition comprises:

1) an oil-in-water emulsion which comprises:
   a) at least one hydrophobic phase comprising an oil and from about 0.1% to about 20%, by weight of the composition, of a light emollient;
   b) at least one hydrophilic phase comprising water, and
   c) an emulsifier having an HLB of at least 6;
2) from about 0.1% to about 5%, by weight of the composition, of a polymeric thickening agent;
3) from about 0.1% to about 2%, by weight of the composition, of a reflective particulate material selected from the group consisting of $TiO_2$, $ZnO$, $ZrO_2$, and mixtures thereof;

wherein the composition has a viscosity of from about 20,000 to about 100,000 and a pH of from about 4 to about 8.

28. A skin care kit according to claim 27 wherein the light emollient is selected from the group consisting of isohexadecane, isododecane, isoeicosane, $C_{9-16}$ isoparaffin, light mineral oil, isopropyl isostearate, methyl isostearate, ethyl isostearate, isononyl isonononoate, octyl palmitate, isopropyl myristate, isopropyl palmitate, diisopropyl sebacate, hexyl laurate, $C_{12-15}$ alcohol benzoate, dioctyl maleate, diisopropyl adipate, $C_{12-15}$ alcohol salicylate, hydrogenated polyisobutene, octyl salicylate, cylomethicone, dimethicone, and mixtures thereof; and the skin care composition comprises:

a) from about 0.1% to about 5%, by weight of the composition, of an emulsifier selected from the group consisting of sorbitan monostearate, sucrose cocoate, steareth-10, steareth-20, steareth-21, steareth-100, oleth-10, oleth-20, laureth-23, cetearyl glucoside, ceteth-10, ceteth-20, PEG-100 stearate, and mixtures thereof; and
b) from about 0.1% to about 20%, by weight of the composition, of niacinamide.

29. A skin care kit comprising a skin care composition contained within a dispenser wherein the skin care composition comprises:

a) an emulsion which comprises:
   1) at least one hydrophobic phase comprising an oil and from about 0.1% to about 20%, by weight of the composition, of a light emollient;
   2) at least one hydrophilic phase comprising water; and
   3) from about 0.1% to about 5%, by weight of the composition, of an emulsifier having an HLB of at least 6;
   4) from about 0.1% to about 2%, by weight of the composition, of a reflective particulate material;
   5) from about 0.1% to about 20%, by weight of the composition, of a vitamin $B_3$ compound; and wherein the composition has a viscosity of from about 15,000 cps to about 200,000 cps and a pH of from about 3 to about 9; and wherein said dispenser comprises a manually-operated pump fixedly connected to an ergonomic container having an actuator cap wherein the dispenser is configured such that the pump is in register with the container and the container is shaped so as to provide for comfortable and easy gripping by a human hand, wherein the hand readily conforms to the shape of the container and the actuator cap may be depressed substantially solely by movement of the tip of either the thumb or index finger; and wherein said pump is suitable for dispensing per activation an amount of said skin care composition sufficient to provide about 2.5 mg/cm$^2$ of skin surface per application.

30. A skin care kit comprising a skin care composition contained within a dispenser wherein the skin care composition comprises:

a) an oil-in-water emulsion which comprises:
   1) at least one hydrophobic phase comprising an oil and from about 0.15% to about 10%, by weight of the composition, of a light emollient selected from the group consisting of isohexadecane, isopropyl isostearate, methyl isostearate, ethyl isostearate, isononyl isonononoate, dimethicone, and mixtures thereof;
   2) at least one hydrophilic phase comprising water; and
   3) from about 0.1% to about 5%, by weight of the composition, of a emulsifier selected from the group consisting of sorbitan monostearate, sucrose cocoate, steareth-10, steareth-20, steareth-21, steareth-100, oleth-10, oleth-20, laureth-23, cetearyl glucoside, ceteth-10, ceteth-20, PEG-100 stearate, and mixtures thereof;
b) from about 0.1% to about 5%, by weight of the composition, of a polymeric thickening agent;
c) from about 0.1% to about 2%, by weight of the composition, of a reflective particulate material selected from the group consisting of $TiO_2$, $ZnO$, $ZrO_2$, and mixtures thereof;
d) from about 0.1% to about 20%, by weight of the composition, of niacinamide;

wherein the composition has a viscosity of from about 25,000 cps to about 60,000 cps and a pH of from about 5 to about 7; and wherein said dispenser comprises a manually-operated pump fixedly connected to an ergonomic container having an actuator cap wherein the dispenser is configured such that the pump is in register with the container and the container is shaped so as to provide for comfortable and easy gripping by a human hand, wherein the hand readily conforms to the shape of the container and the actuator cap may be depressed substantially solely by movement of the tip of either the thumb or index finger; and wherein said pump is suitable for dispensing per activation an amount of said skin care composition sufficient to provide about 2.5 $mg/cm^2$ of skin surface per application.

* * * * *

UNITED STATES PATENT AND TRADEMARK OFFICE
CERTIFICATE OF CORRECTION

PATENT NO. : 6,013270
DATED : January 11, 2000
INVENTOR(S) : Peter James Hargraves, et. al.

It is certified that error appears in the above-identified patent and that said Letters Patent is hereby corrected as shown below:

At column 2, line 26 "water," should read --water;--.

At column 2, line 38 "thereof, and" should read --thereof; and--.

At column 4, line 52 "ensues" should read --ensures--.

At column 6, line 45 "mono-." should read --mono-,--

At column 6, line 48 "PEG6" should read --PEG-6--.

At column 11, line 12 "steareth6" should read --steareth-6--.

At column 21, line 2 "water, and" should read --water; and--.

At column 21, line 57 "*Dosape*" should read --*Dosage*--.

At column 22, line 37 "thereof with" should read --thereof, with--.

At column 25, line 16 "(A)$_j$B)$_m$(C)$_n$" should read --(A)$_i$(B)$_m$(C)$_n$--.

At column 27, line 52 "text discontinuities" should read --textural discontinuities--.

At column 28, line 6 "250 mn" should read --250 nm--.

At column 34, line 11 "ChatteJee" should read --Chatterjee--

At column 34, line 62 "castor oil cocoa" should read --castor oil, cocoa--.

At column 36, line 41 "ether, hydroquinone" should read --ether; hydroquinone --.

At column 36, line 54 "2cyano" should read --2-cyano--.

At column 37, line 13 "2-etlylhexyl" should read --2-ethylhexyl--.

At column 44, line 5 "water, and" should read --water; and--.

Signed and Sealed this

Eighth Day of May, 2001

*Attest:*

*Attesting Officer*

NICHOLAS P. GODICI

*Acting Director of the United States Patent and Trademark Office*